US012178648B2

(12) United States Patent
Fife et al.

(10) Patent No.: US 12,178,648 B2
(45) Date of Patent: Dec. 31, 2024

(54) METHODS AND APPARATUSES FOR PACKAGING AN ULTRASOUND-ON-A-CHIP

(71) Applicant: BFLY Operations, Inc., Guilford, CT (US)

(72) Inventors: Keith G. Fife, Palo Alto, CA (US); Jianwei Liu, Fremont, CA (US); Andrew Betts, Guilford, CT (US)

(73) Assignee: BFLY OPERATIONS, INC, Burlington, MA (US)

( * ) Notice: Subject to any disclaimer, the term of this patent is extended or adjusted under 35 U.S.C. 154(b) by 80 days.

(21) Appl. No.: 17/853,835

(22) Filed: Jun. 29, 2022

(65) Prior Publication Data

US 2022/0395254 A1    Dec. 15, 2022

Related U.S. Application Data

(63) Continuation of application No. 16/260,242, filed on Jan. 29, 2019, now Pat. No. 11,389,137.
(Continued)

(51) Int. Cl.
*B06B 1/06*       (2006.01)
*A61B 8/00*       (2006.01)
(Continued)

(52) U.S. Cl.
CPC .............. *A61B 8/4483* (2013.01); *A61B 8/54* (2013.01); *A61B 8/56* (2013.01); *B06B 1/0622* (2013.01);
(Continued)

(58) Field of Classification Search
CPC .................................................... B06B 1/0622
See application file for complete search history.

(56) References Cited

U.S. PATENT DOCUMENTS 9,067,779 B1    6/2015   Rothberg et al.
9,242,275 B2    1/2016   Rothberg et al.
(Continued)

FOREIGN PATENT DOCUMENTS

CN    106536067 A    3/2017
EP    2 881 182 A2   6/2015
(Continued)

OTHER PUBLICATIONS

*EP19747685.6, Oct. 7, 2021, Extended European Search Report.
(Continued)

*Primary Examiner* — Bryan P Gordon
(74) *Attorney, Agent, or Firm* — Boston & Galway

(57) ABSTRACT

Aspects of the disclosure described herein related to packaging an ultrasound-on-a-chip. In some embodiments, an apparatus includes an ultrasound-on-a-chip that has through-silicon vias (TSVs) and an interposer coupled to the ultrasound-on-a-chip and including vias, where the ultrasound-on-a-chip is coupled to the interposer such that the TSVs in the ultrasound-on-a-chip are electrically connected to the vias in the interposer. In some embodiments, an apparatus includes an ultrasound-on-a-chip having bond pads, an interposer that has bond pads and that is coupled to the ultrasound-on-a-chip, and wirebonds extending from the bond pads on the ultrasound-on-a-chip to the bond pads on the interposer.

15 Claims, 29 Drawing Sheets

Related U.S. Application Data

(60) Provisional application No. 62/623,948, filed on Jan. 30, 2018.

(51) Int. Cl.
  *B81B 7/00* (2006.01)
  *B81C 1/00* (2006.01)
  *H10N 30/03* (2023.01)

(52) U.S. Cl.
  CPC ........ *B81B 7/0048* (2013.01); *B81C 1/00261* (2013.01); *H10N 30/03* (2023.02)

(56) References Cited

U.S. PATENT DOCUMENTS

| | | | |
|---|---|---|---|
| 9,394,162 | B2 | 7/2016 | Rothberg et al. |
| 9,499,392 | B2 | 11/2016 | Rothberg et al. |
| 9,910,017 | B2 | 3/2018 | Rothberg et al. |
| 9,910,018 | B2 | 3/2018 | Rothberg et al. |
| 10,175,206 | B2 | 1/2019 | Rothberg et al. |
| 10,228,353 | B2 | 3/2019 | Rothberg et al. |
| 10,247,708 | B2 | 4/2019 | Rothberg et al. |
| 11,389,137 | B2 | 7/2022 | Fife et al. |
| 2008/0183078 | A1 | 7/2008 | Haider et al. |
| 2008/0315331 | A1 | 12/2008 | Wodnicki et al. |
| 2011/0055447 | A1 | 3/2011 | Costa |
| 2011/0316147 | A1 | 12/2011 | Shih et al. |
| 2012/0133001 | A1* | 5/2012 | Tkaczyk .............. A61B 8/4483 438/66 |
| 2012/0133054 | A1* | 5/2012 | Tkaczyk ................. G01T 1/243 438/57 |
| 2014/0044388 | A1 | 2/2014 | Su et al. |
| 2016/0009544 | A1* | 1/2016 | Rothberg ................ H01L 24/94 257/737 |
| 2016/0009549 | A1 | 1/2016 | Rothberg et al. |
| 2016/0181174 | A1* | 6/2016 | Gambino ............. H01L 23/481 438/666 |
| 2016/0280538 | A1 | 9/2016 | Rothberg et al. |
| 2016/0290969 | A1 | 10/2016 | Rothberg et al. |
| 2016/0290970 | A1 | 10/2016 | Rothberg et al. |
| 2017/0047309 | A1 | 2/2017 | Baek et al. |
| 2017/0315099 | A1 | 11/2017 | Rothberg et al. |
| 2017/0360397 | A1 | 12/2017 | Rothberg et al. |
| 2017/0360405 | A1 | 12/2017 | Rothberg et al. |
| 2017/0360413 | A1 | 12/2017 | Rothberg et al. |
| 2018/0003678 | A1 | 1/2018 | Rothberg et al. |
| 2018/0257927 | A1* | 9/2018 | Rothberg ................ B81B 7/008 |
| 2018/0364201 | A1 | 12/2018 | Rothberg et al. |
| 2018/0369862 | A1 | 12/2018 | Alie et al. |
| 2019/0142387 | A1 | 5/2019 | Chen et al. |
| 2019/0231312 | A1 | 8/2019 | Fife et al. |
| 2019/0336103 | A1* | 11/2019 | Fife ...................... B06B 1/0622 |

FOREIGN PATENT DOCUMENTS

| | | |
|---|---|---|
| FR | 2 917 841 A1 | 12/2008 |
| JP | 2003297966 A | 10/2003 |
| JP | 2007129191 A | 5/2007 |
| JP | 2009044718 A | 2/2009 |
| JP | 2009065009 A | 3/2009 |
| JP | 2017-12729 A | 1/2017 |
| JP | 2017069652 A | 4/2017 |
| WO | WO 2012/075153 A2 | 6/2012 |

OTHER PUBLICATIONS

*PCT/US2019/015518, Apr. 12, 2019, International Search Report and Written Opinion.
*PCT/US2019/015518, Aug. 13, 2020, International Preliminary Report on Patentability.
Office Action issued in counterpart Chinese Application No. 201980010690.X; Dated Feb. 16, 2023 (9 pages).
Extended European Search Report for European Application No. 19747685.6, dated Oct. 7, 2021.
International Search Report and Written Opinion mailed Apr. 12, 2019 in connection with International Application No. PCT/US2019/015518.
International Preliminary Report on Patentability mailed Aug. 13, 2020 in connection with International Application No. PCT/US2019/015518.
Office Action issued in corresponding Japanese Patent Application No. 2020-540804, mailed Jan. 27, 2023 (6 pages).
Notice of Preliminary Rejection issued in counterpart Korean Application No. 10-2020-7024309 dated Dec. 19, 2023 (12 pages).

* cited by examiner

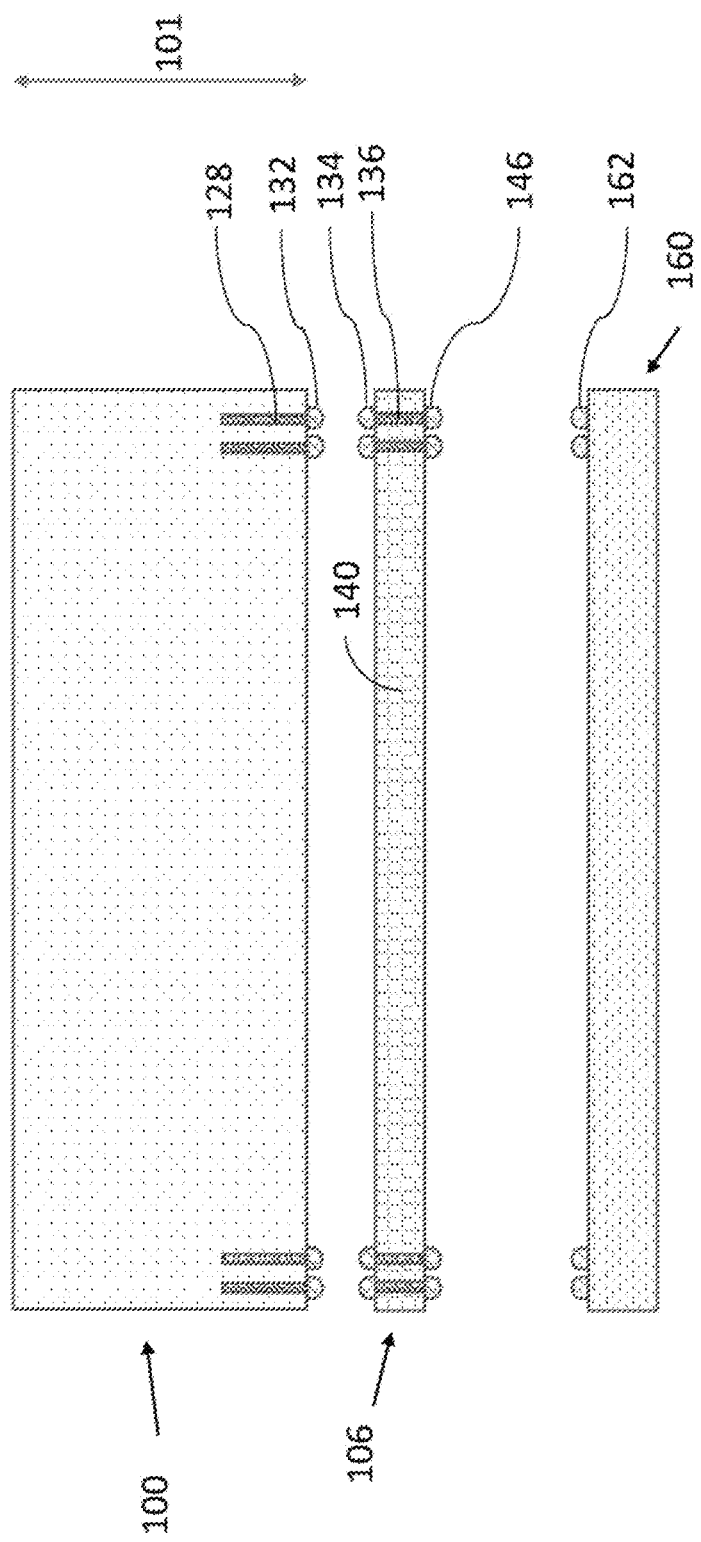

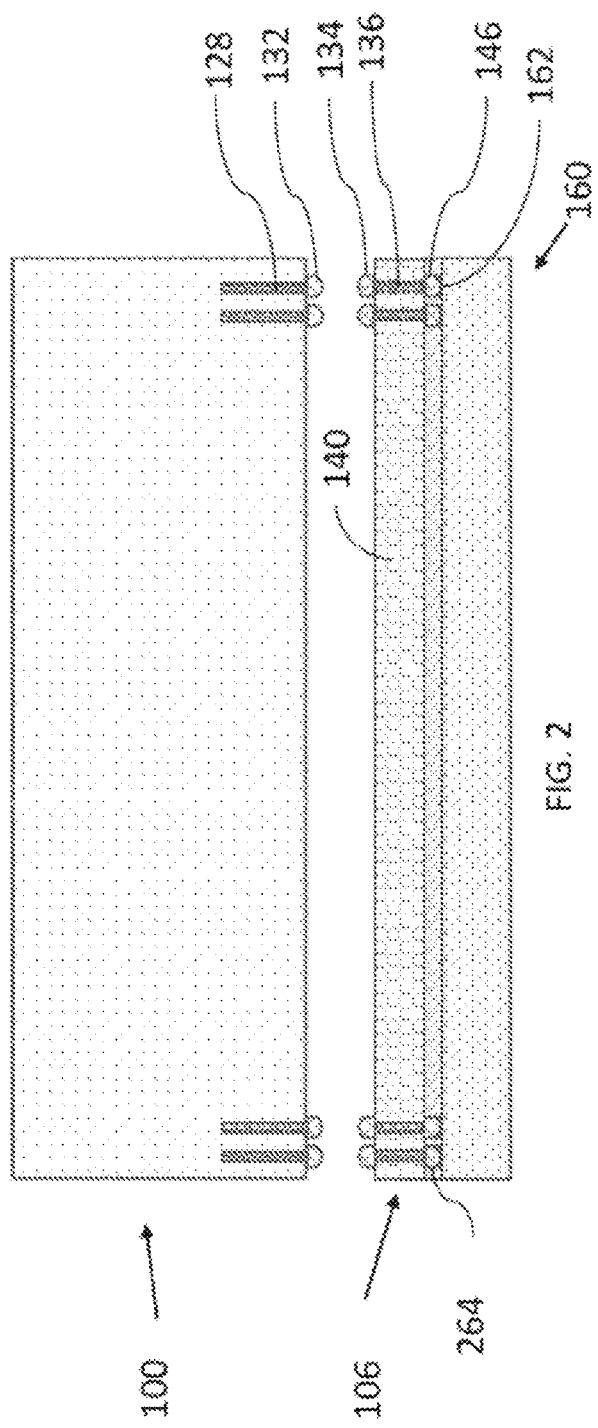
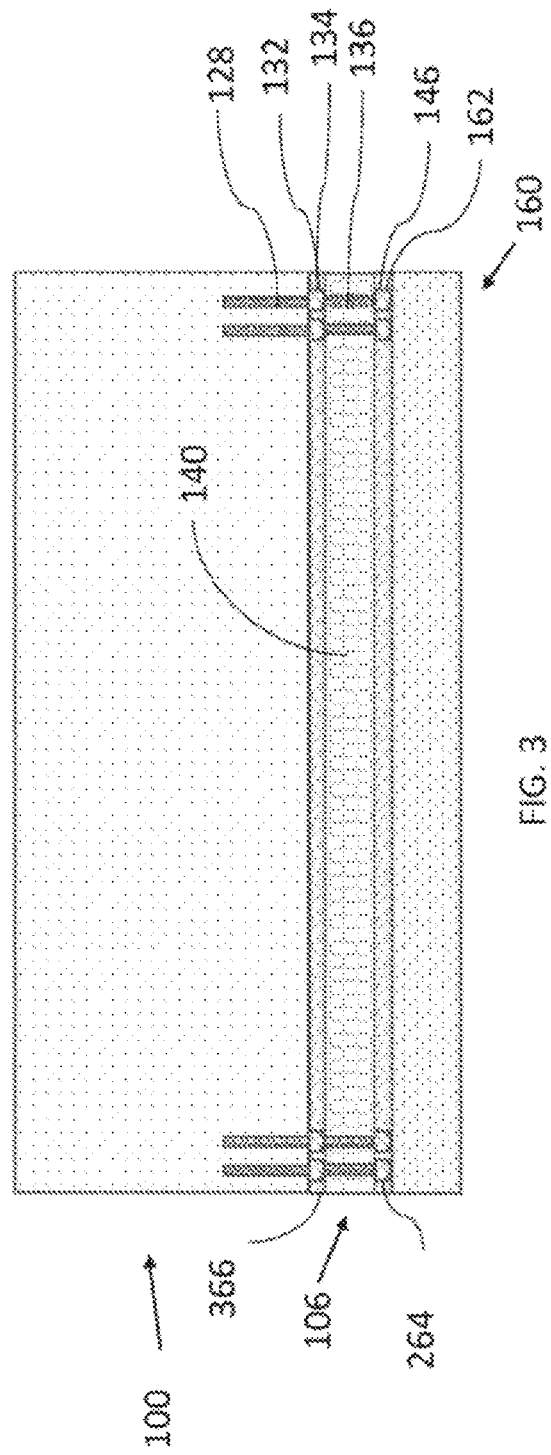

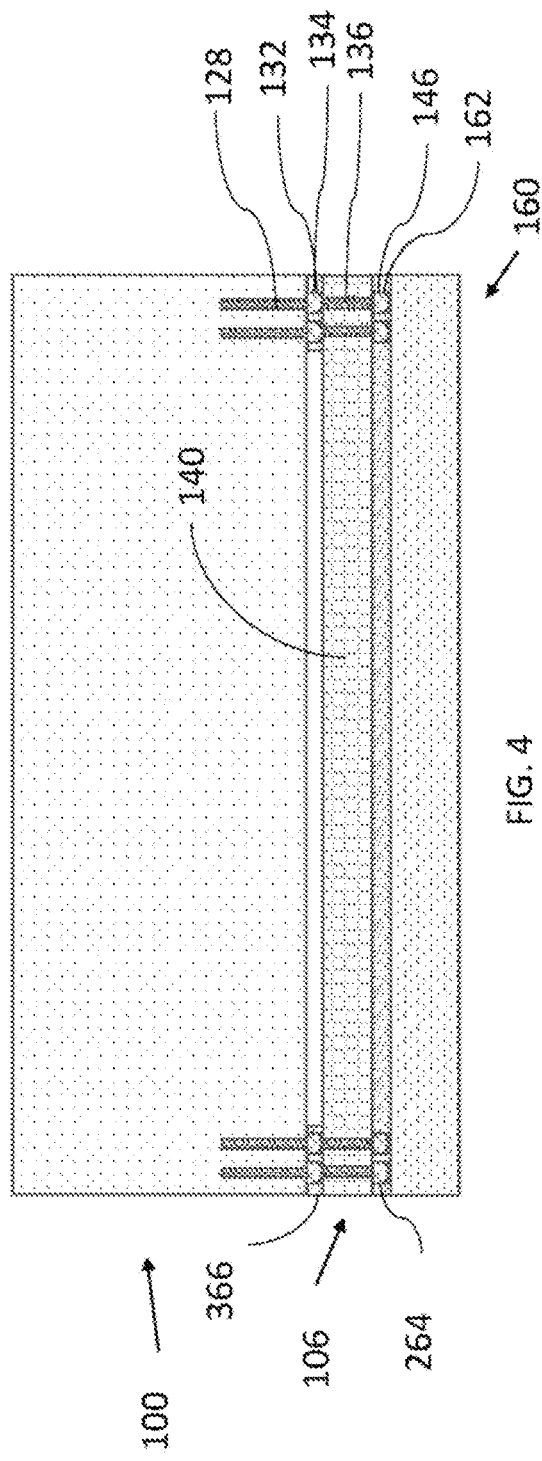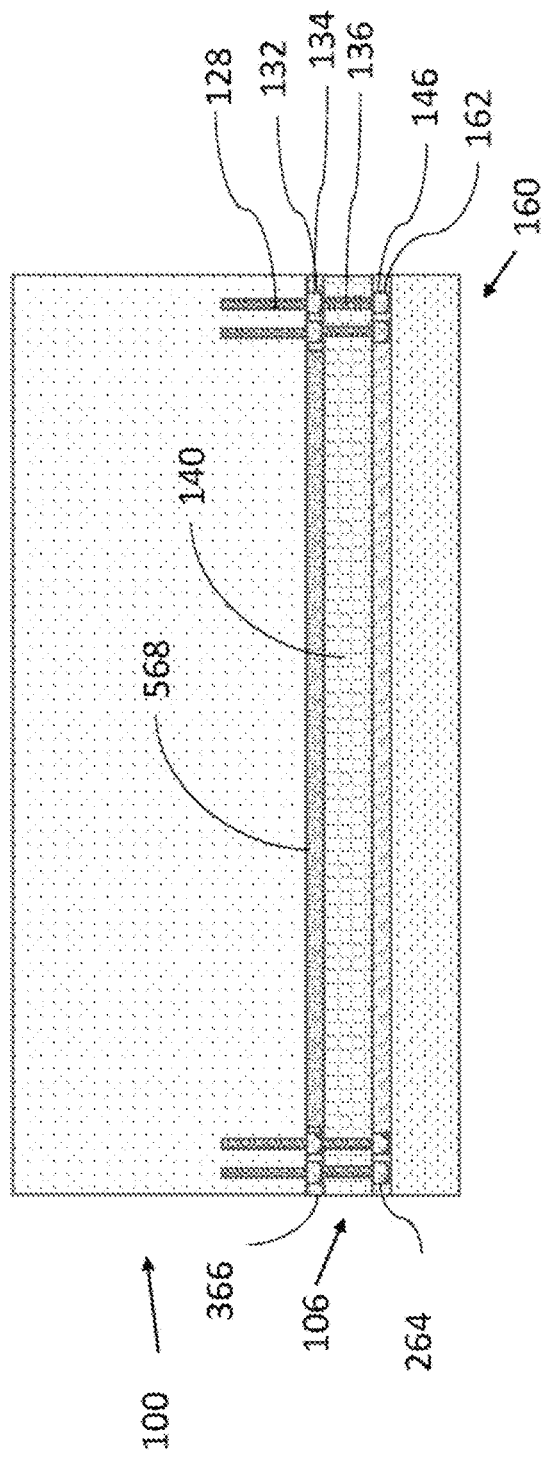

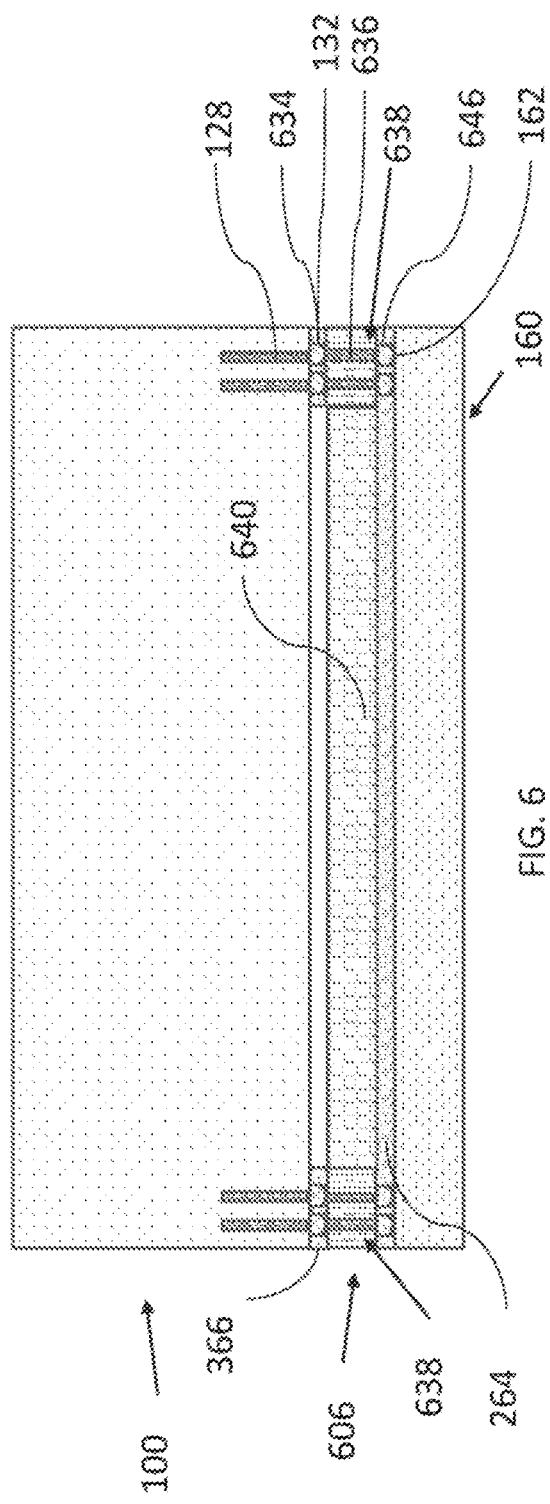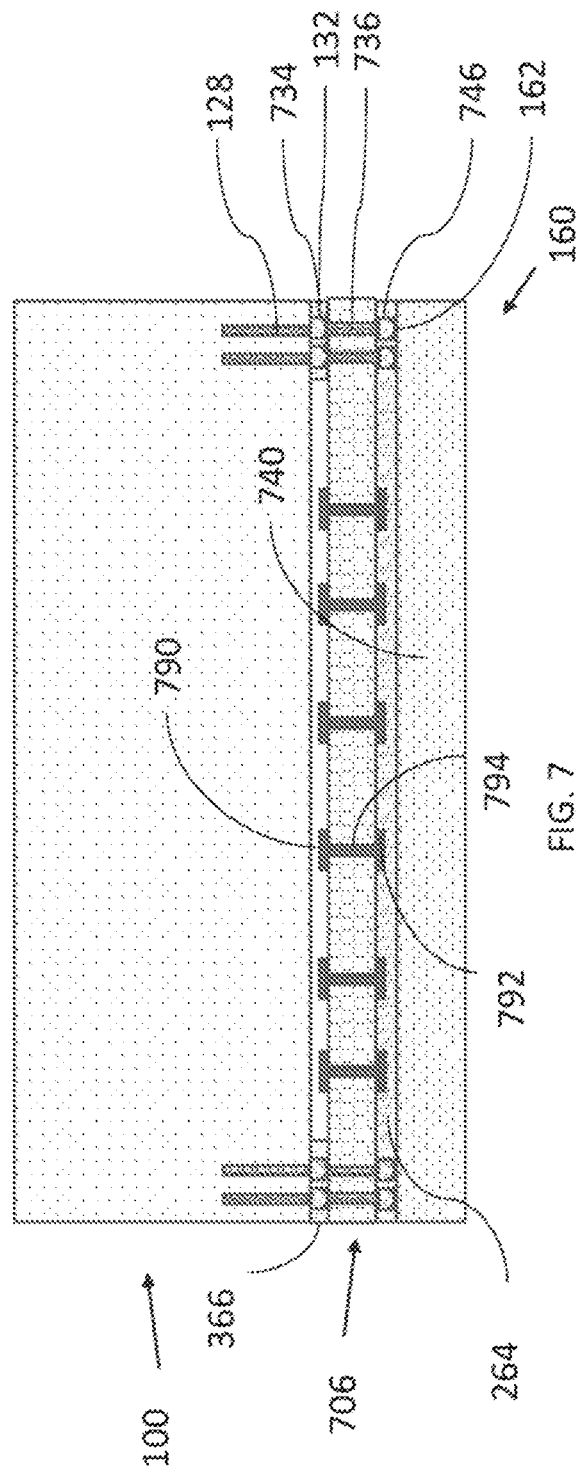

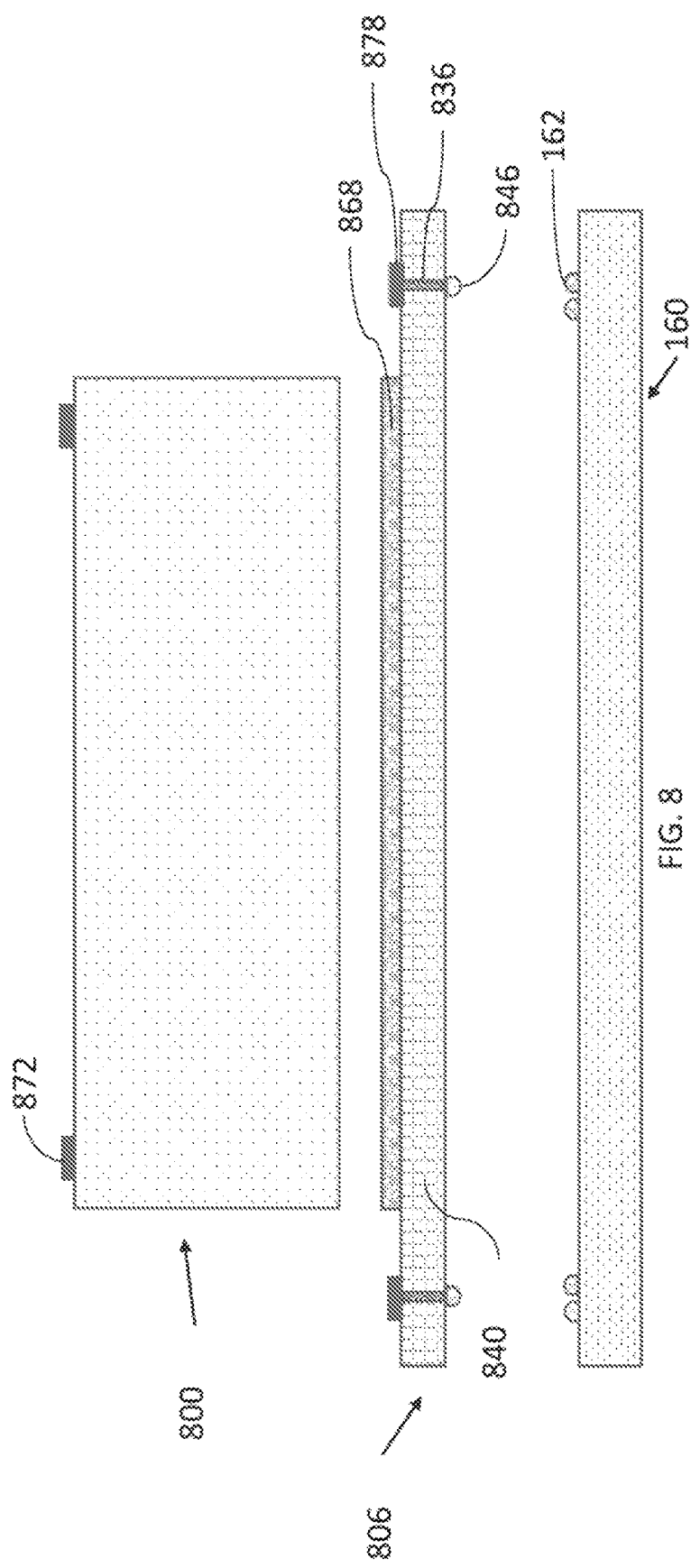

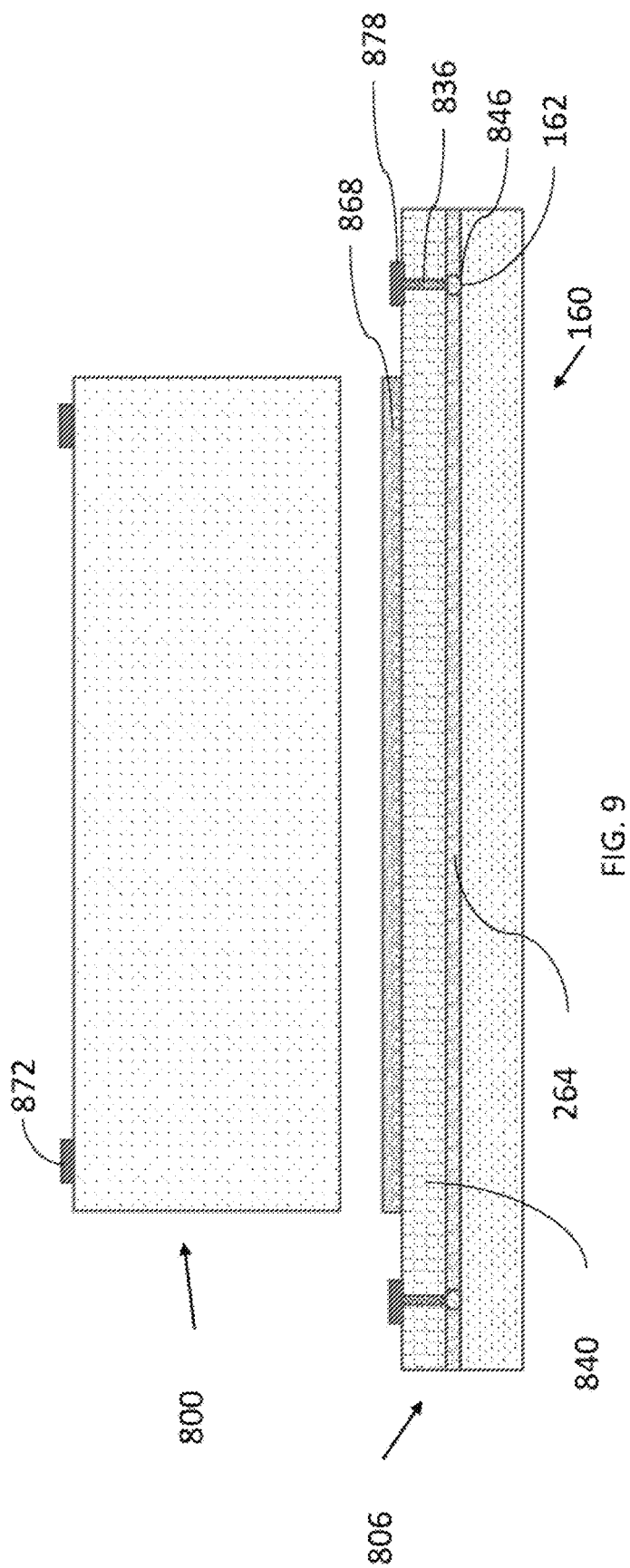

METHODS AND APPARATUSES FOR PACKAGING AN ULTRASOUND-ON-A-CHIP

CROSS-REFERENCE TO RELATED APPLICATIONS

This Application is a continuation claiming the benefit under 35 U.S.C. § 120 of U.S. application Ser. No. 16/260,242, filed Jan. 29, 2019, and entitled "METHODS AND APPARATUSES FOR PACKAGING AN ULTRASOUND-ON-A-CHIP", which is hereby incorporated herein by reference in its entirety.

U.S. application Ser. No. 16/260,242 claims the benefit under 35 U.S.C. § 119(e) of U.S. Provisional Patent Application Ser. No. 62/623,948, filed Jan. 30, 2018, and entitled "METHODS AND APPARATUSES FOR PACKAGING AN ULTRASOUND-ON-A-CHIP," which is hereby incorporated herein by reference in its entirety.

FIELD

Generally, the aspects of the technology described herein relate to ultrasound systems. Some aspects relate to packaging an ultrasound-on-a-chip.

BACKGROUND

Ultrasound devices may be used to perform diagnostic imaging and/or treatment, using sound waves with frequencies that are higher with respect to those audible to humans. Ultrasound imaging may be used to see internal soft tissue body structures, for example to find a source of disease or to exclude any pathology. When pulses of ultrasound are transmitted into tissue (e.g., by using an ultrasound imaging device), sound waves are reflected off the tissue, with different tissues reflecting varying degrees of sound. These reflected sound waves may then be recorded and displayed as an ultrasound image to the operator. The strength (amplitude) of the sound signal and the time it takes for the wave to travel through the body provide information used to produce the ultrasound image. Many different types of images can be formed using ultrasound devices, including real-time images. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

According to one aspect, an apparatus includes an ultrasound-on-a-chip including through-silicon vias (TSVs) and an interposer coupled to the ultrasound-on-a-chip and including vias, where the ultrasound-on-a-chip is coupled to the interposer such that the TSVs in the ultrasound-on-a-chip are electrically connected to the vias in the interposer.

In some embodiments, a thickness of the ultrasound-on-a-chip is about 200 microns to about 300 microns. In some embodiments, the interposer includes a heat sink portion. In some embodiments, the heat sink portion includes ceramic material. In some embodiments, the ceramic material is aluminum nitride. In some embodiments, the interposer further includes an electrical connectivity portion that includes the vias. In some embodiments, the electrical connectivity portion includes an organic, glass, and/or silicon material. In some embodiments, the interposer includes copper patterns protruding towards the ultrasound-on-a-chip from a face of the interposer. In some embodiments, the ultrasound-on-a-chip and the interposer are coupled together using a surface-mount technology (SMT) process. In some embodiments, underfill is disposed along substantially all of an interface between the ultrasound-on-a-chip and the interposer. In some embodiments, an adhesive is disposed along a portion of an interface between the ultrasound-on-a-chip and the interposer. In some embodiments, an empty space exists along a portion of an interface between the ultrasound-on-a-chip and the interposer. In some embodiments, a size of an upper face of the ultrasound-on-a-chip is approximately the same as a size of an upper face of the apparatus. In some embodiments, the apparatus further includes a printed circuit board including circuitry and/or traces, the printed circuit board being coupled to the interposer such that the vias in the interposer are electrically connected to the circuitry and/or traces in the printed circuit board.

According to another aspect, an apparatus includes an ultrasound-on-a-chip including first bond pads, an interposer including second bond pads and coupled to the ultrasound-on-a-chip, and wirebonds extending from the first bond pads on the ultrasound-on-a-chip to the second bond pads on the interposer.

In some embodiments, a thickness of the ultrasound-on-a-chip is about 200 microns to about 300 microns. In some embodiments, the interposer includes a heat sink portion. In some embodiments, the heat sink portion includes ceramic material. In some embodiments, the ceramic material is aluminum nitride. In some embodiments, the interposer further includes an electrical connectivity portion that includes the vias. In some embodiments, the electrical connectivity portion includes an organic, glass, and/or silicon material. In some embodiments, the interposer includes copper patterns protruding towards the ultrasound-on-a-chip from a face of the interposer. In some embodiments, the ultrasound-on-a-chip and the interposer are coupled together through an adhesive. In some embodiments, the apparatus further includes a printed circuit board including circuitry and/or traces, the interposer further includes vias, and the printed circuit board is coupled to the interposer such that the vias in the interposer are electrically connected to the circuitry and/or traces in the printed circuit board.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

FIG. 1 illustrates a cross-sectional view of an example ultrasound device during packaging, in accordance with certain embodiments described herein;

FIG. 2 illustrates another cross-sectional view of the example ultrasound device of FIG. 1 during packaging, in accordance with certain embodiments described herein;

FIG. 3 illustrates another cross-sectional view of the example ultrasound device of FIG. 1 during packaging, in accordance with certain embodiments described herein;

FIG. 4 illustrates a cross-sectional view of another example ultrasound device, in accordance with certain embodiments described herein;

FIG. 5 illustrates a cross-sectional view of another example ultrasound device, in accordance with certain embodiments described herein;

FIG. 6 illustrates a cross-sectional view of another example ultrasound device, in accordance with certain embodiments described herein;

FIG. 7 illustrates a cross-sectional view of another example ultrasound device, in accordance with certain embodiments described herein;

FIG. 8 illustrates a cross-sectional view of an example ultrasound device during packaging, in accordance with certain embodiments described herein;

FIG. 9 illustrates another cross-sectional view of the example ultrasound device of FIG. 8 during packaging, in accordance with certain embodiments described herein;

DETAILED DESCRIPTION

Figure 10:
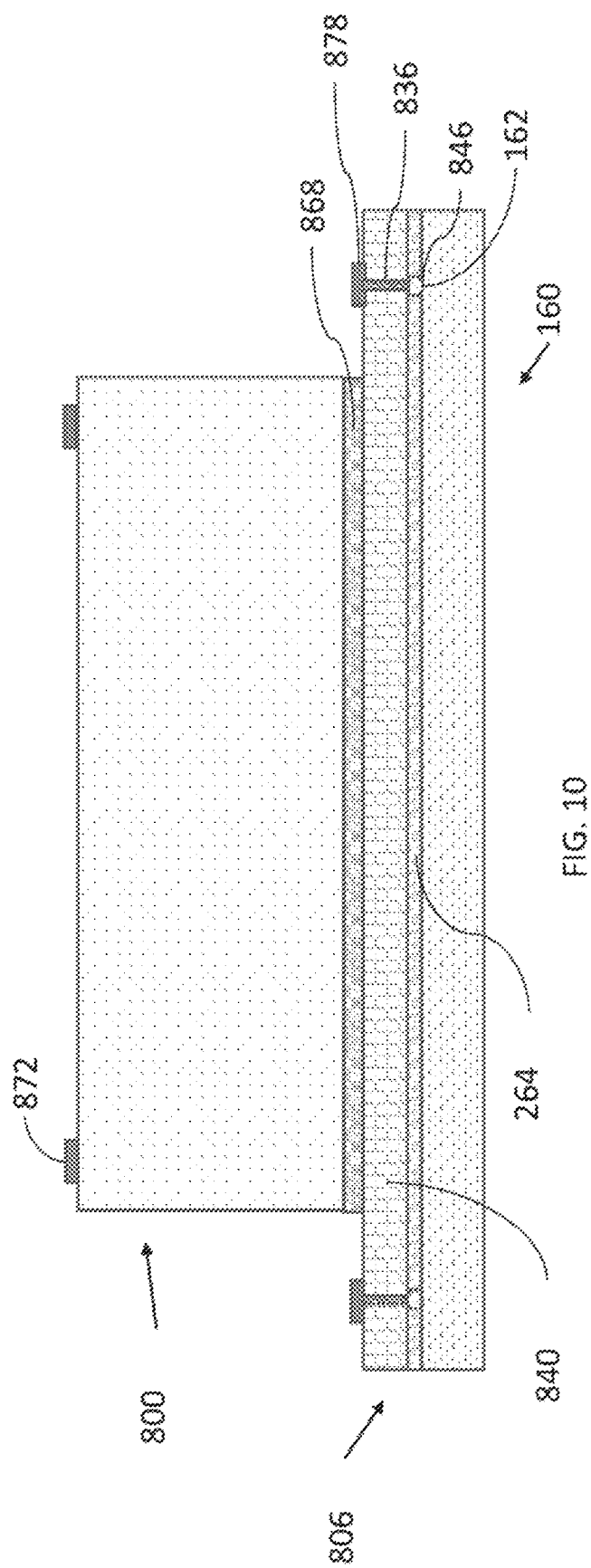
FIG. 10 illustrates another cross-sectional view of the example ultrasound device of FIG. 8 during packaging, in accordance with certain embodiments described herein.

Conventional ultrasound systems are large, complex, and expensive systems that are typically only purchased by large medical facilities with significant financial resources. Recently, less expensive, portable, and less complex ultrasound imaging devices have been introduced. Such imaging devices may include ultrasonic transducers monolithically integrated onto a single semiconductor ultrasound-on-a-chip to form a monolithic ultrasound device. Aspects of such ultrasound-on-a chip devices are described in U.S. patent application Ser. No. 15/415,434 titled "UNIVERSAL ULTRASOUND DEVICE AND RELATED APPARATUS AND METHODS," filed on Jan. 25, 2017 (and assigned to the assignee of the instant application) and published as U.S. Pat. Publication No. 2017/0360397, which is incorporated by reference herein in its entirety.

The inventors have recognized features that may be helpful for packaging such ultrasound-on-a-chips. Some features may help with electrical, thermal, and/or acoustic considerations associated with ultrasound devices. For example, the inventors have recognized that implementing through-silicon vias (TSVs) in an ultrasound-on-a-chip for electrically connecting the ultrasound-on-a-chip to the external environment may be helpful for a number of reasons that will be described below. The inventors have also recognized that it may be helpful to couple an ultrasound-on-a-chip to a heat sink. For example, the heat sink may include ceramic material, such as aluminum nitride. In embodiments in which the ultrasound-on-a-chip includes TSVs, the heat sink may include vias, or be a portion of a device that includes vias. In such embodiments, the heat sink, or the device that includes the heat sink, may be considered an interposer, in that the interposer routes electrical signals from the ultrasound-on-a-chip. In some embodiments, the interposer may include a heat sink portion and an electrical connectivity portion. The electrical connectivity portion may be made of organic, glass, or silicon material, and may include electrical vias passing through from its top to bottom surface. Such an interposer may be considered a hybrid interposer in that it includes a separate electrical connectivity portion and a separate heat sink portion, and may be considered an integrated solution for providing both an electrical connectivity solution and a thermal solution. Whether the vias of the interposer pass through a heat sink or an electrical connectivity portion of a hybrid interposer, the TSVs of the ultrasound-on-a-chip may be electrically connected to the vias of the interposer, and the interposer may be coupled to a printed circuit board (PCB), such that the interposer routes electrical signals from the ultrasound-on-a-chip to the PCB. In embodiments in which the heat sink to which the ultrasound-on-a-chip is coupled includes ceramic material, the ceramic material may have an acceptably high thermal conductivity that enables it to function as a heat sink for the ultrasound-on-a-chip. Furthermore, the ceramic material may have a thermal expansion coefficient that matches the thermal expansion coefficient of silicon to an acceptable degree, which may reduce warping of the ultrasound-on-a-chip (which includes silicon) and the interposer to an acceptable degree.

TSVs in the ultrasound-on-a-chip device may be helpful for the following reasons:

1. Compared with other interconnect for electrically connecting the ultrasound-on-a-chip to the external environment that may require longer electrical paths, TSVs may present lower parasitic inductance and resistance, leading to higher power efficiency and less heating of the ultrasound device.

2. Using TSVs may facilitate using a surface mount technology (SMT) process for coupling the ultrasound-on-a-chip to an interposer. It may be possible to solder bond most or all of the solder bumps of the interposer to the solder bumps of the ultrasound-on-a-chip at once, and it may be possible to use a single machine to solder bond multiple ultrasound-on-a-chips to multiple interposers at once. In other words, using TSVs may facilitate a high throughput packaging process that may be better suited for packaging high volumes of ultrasound-on-a-chips.

3. During ultrasound imaging, the upper face of the ultrasound-on-a-chip may be pressed against a subject. (It should be noted that one or more structures, such as an acoustic lens, may be disposed between the upper face of the ultrasound-on-a-chip and the subject during imaging.) The TSVs are not disposed near the upper face of the ultrasound-on-a-chip and accordingly may be less subject to damage due to this pressure.

4. Other interconnect structures for electrically connecting to the ultrasound-on-a-chip may extend laterally from the upper face of the ultrasound-on-a-chip. Accordingly, the upper face of the packaged ultrasound-on-a-chip may be larger in size than the upper face of the ultrasound-on-a-chip itself due to this lateral extension. (To measure these sizes, one may look downwards from a bird's-eye view at the packaged ultrasound-on-a-chip. The size of the upper face of the packaged ultrasound-on-a-chip may be the total area of the packaged ultrasound-on-a-chip visible from a bird's-eye view when looking downwards at the ultrasound-on-a-chip. The size of the upper face of the ultrasound-on-a-chip may be the area of just the ultrasound-on-a-chip visible from a bird's-eye view when looking downwards at the ultrasound-on-a-chip, excluding any interconnect or other packaging.) As discussed above, TSVs are not disposed near the upper face of the ultrasound-on-a-chip, and therefore do not contribute significantly to the size of the upper face of the ultrasound-on-a-chip. In some embodiments, the size of the upper face of the packaged ultrasound-on-a-chip may be approximately the same as the size of the upper face of the unpackaged ultrasound on a chip. (For example, the size of the upper face of the packaged ultrasound-on-a-chip may between or including 100%-101%, 100%-105%, 100%-110%, 100%-120%, 100%-125%, 100%-130%, 100%-140%, or 100%-150% of the size of the upper face of the unpackaged ultrasound-on-a-chip).

Avoiding increasing the size of the upper face of the packaged ultrasound-on-a-chip with interconnects may help to reduce the overall size of the ultrasound device and enable form factors for the ultrasound device such as ultrasound patches. Reducing the overall size of the ultrasound device may also reduce costs in producing the ultrasound device.

Additionally, avoiding increasing the size of the upper face of the packaged ultrasound-on-a-chip with interconnect may, for example, help the upper face of the packaged ultrasound-on-a-chip fit between a subject's ribs during imaging. This may be especially helpful for cardiac imaging. Additionally, avoiding increasing the size of the upper face of the packaged ultrasound-on-a-chip with interconnect may help to reduce the amount of acoustic lens material that is deposited on the upper face of the packaged ultrasound-on-a-chip. In particular, reducing the thickness of the acoustic lens material may help to reduce attenuation of pressure waves generated by the ultrasound device.

Some embodiments of the ultrasound-on-a-chip may not include TSVs. In such embodiments, wirebonds extending from the ultrasound-on-a-chip may route signals from the ultrasound-on-a-chip to a PCB. In some embodiments, the wirebonds from the ultrasound-on-a-chip may extend to an interposer that is coupled to the ultrasound-on-a-chip and to a PCB. The interposer may be one of the embodiments described above that includes via that are electrically connected to the PCB. Wirebonds extending from the ultrasound-on-a-chip to the interposer may be shorter than wirebonds extending from the ultrasound-on-a-chip to the PCB. The shorter wirebonds may result in a smaller upper face of the packaged ultrasound-on-a-chip which, as described above, may help to reduce the overall size of the ultrasound device, may help the upper face of the packaged ultrasound-on-a-chip fit between a subject's ribs during imaging, and may help to reduce the amount of acoustic lens material that is deposited on the upper face of the packaged ultrasound-on-a-chip. In some embodiments, wirebonds from the ultrasound-on-a-chip may extend to the PCB. In such embodiments, a heat sink coupled to the ultrasound-on-a-chip may not include vias.

The inventors have also recognized that it may be helpful to reduce the ultrasound-on-a-chip in thickness. In some embodiments, an ultrasound device that includes a thinned ultrasound-on-a-chip may force long-wavelength components of ultrasound waves to exit the ultrasound-on-a-chip at the interface between the ultrasound-on-a-chip and the interposer, thus reducing spurious acoustic reflections back into the ultrasound-on-a-chip and interference. Acoustic matching (e.g., using a backing material) at the interface between the ultrasound-on-a-chip and the interposer may not be required to force the long-wavelength components of ultrasound waves to exit, if the ultrasound-on-a-chip has been thinned as described. In some embodiments, the ultrasound-on-a-chip may not be thinned, which may facilitate easier handling of the ultrasound-on-a-chip during packaging.

It should be appreciated that the embodiments described herein may be implemented in any of numerous ways. Examples of specific implementations are provided below for illustrative purposes only. It should be appreciated that these embodiments and the features/capabilities provided may be used individually, all together, or in any combination of two or more, as aspects of the technology described herein are not limited in this respect.

FIGS. 1-3 illustrate cross-sectional views of an example ultrasound device during packaging, in accordance with certain embodiments described herein. FIG. 1 illustrates an ultrasound-on-a-chip 100, an interposer 106, and a printed circuit board (PCB) 160. The ultrasound-on-a-chip 100 includes through-silicon vias (TSVs) 128 and solder bumps 132. Other components of the ultrasound-on-a-chip 100, such as integrated circuitry and ultrasonic transducers, are not shown for simplicity. The interposer 106 includes a heat sink portion 140, vias 136, solder bumps 134, and solder bumps 146. The PCB 160 includes solder bumps 162. It should be appreciated that the ultrasound-on-a-chip 100 (and all other ultrasound-on-a-chip described herein) may have more TSVs 128 and solder bumps 132 than shown, the interposer 106 (and all other interposers described herein) may have more vias 136, solder bumps 134, and solder bumps 146 than shown, and the PCB 160 (and all other PCBs described herein) may have more solder bumps 162 than shown.

The TSVs 128 of the ultrasound-on-a-chip 100 are vias that may pass through a bulk silicon layer (not shown in FIG. 1) of the ultrasound-on-a-chip 100. The TSVs 128 may electrically connect one or more integrated circuits and/or interconnect (not shown in FIG. 1) in the ultrasound-on-a-chip 100 to the solder bumps 132, which are on a lower surface of the ultrasound-on-a-chip 100 and may be external electrical contacts. The TSVs 128 may be formed for example, from copper, doped polysilicon, or tungsten. An example of the ultrasound-on-a-chip 100 may be found in FIG. 29. Additional information regarding ultrasound-on-a-chips may be found, for example, in U.S. Pat. No. 9,067,779 titled "MICROFABRICATED ULTRASONIC TRANSDUCERS AND RELATED APPARATUS AND METHODS," granted on Jun. 30, 2015 (and assigned to the assignee of the instant application) which is incorporated by reference herein in its entirety.

In the ultrasound device of FIG. 1, the height 101 of the ultrasound-on-a-chip 100 has been reduced after having been fabricated (e.g., using grinding or etching), prior to packaging. In such embodiments, the height of the ultrasound-on-a-chip 100 may be reduced from between or equal to approximately 760-800 microns to between or equal to approximately 200-300 microns. Thinning the ultrasound-on-a-chip 100 may help, during use, to force long-wavelength components of ultrasound waves to exit the ultrasound-on-a-chip 100 at the interface between the ultrasound-on-a-chip 100 and the interposer 106, thus reducing spurious acoustic reflections back into the ultrasound-on-a-chip 100 and interference. Acoustic matching (e.g., using a backing material) at the interface between the ultrasound-on-a-chip 100 and the interposer 106 may not be required to force the long-wavelength components of ultrasound waves to exit, if the ultrasound-on-a-chip 100 has been thinned as described.

The heat sink portion 140 of the interposer 106 may include a ceramic material, such as aluminum nitride, aluminum oxide, beryllium, and/or low-temperature co-fired ceramic (LTCC). The heat sink portion 140 may help to conduct heat away from the ultrasound-on-a-chip 100. For example, ceramic material may have an acceptably high thermal conductivity that enables it to function as a heat sink for the ultrasound-on-a-chip 100. Furthermore, the ceramic material may have a thermal expansion coefficient that matches the thermal expansion coefficient of silicon to an acceptable degree, which may reduce warping of the ultrasound-on-a-chip 100 (which includes silicon) and the interposer 106 to an acceptable degree.

The solder bumps 134 are on an upper surface of the interposer 106 and the solder bumps 146 are on a lower surface of the interposer 106. The vias electrically connect the solder bumps 134 to the solder bumps 146. The vias 136 may be formed by laser drilling and plating.

The PCB 160 may include, for example, FR4 or BT. The solder bumps 162 are on the upper surface of the PCB 160 and may electrically connect to traces and/or circuitry (not shown in FIG. 1) on or within the PCB 160.

In FIG. 2, the interposer 106 and the PCB 160 are coupled together. The interposer 106 may be bonded to the PCB 160 using a surface-mount technology (SMT) process. In particular, the solder bumps 146 on the lower surface of the interposer 106 may be solder bonded to the solder bumps 162 on the upper surface of the PCB 160. Therefore, circuitry and/or traces in the PCB 160 may be electrically connected, through the solder bumps 162 and 146 and the vias 136 to the solder bumps 134 on the upper surface of the interposer 106. FIG. 2 further illustrates underfill 264 that has been deposited between the interposer 106 and the PCB 160. The underfill 264 may help improve the mechanical and thermal properties of the solder bonds between the interposer 106 and the PCB 160.

In FIG. 3, the ultrasound-on-a-chip 100 and the interposer 106 are coupled together. The ultrasound-on-a-chip 100 may be bonded to the interposer 106 using a surface-mount technology (SMT) process. In particular, the solder bumps 134 on the upper surface of the interposer 106 may be solder bonded to the solder bumps 132 on the lower surface of the ultrasound-on-a-chip 100. Therefore, integrated circuitry and/or interconnect in the ultrasound-on-a-chip 100 may be electrically connected, through the TSVs 128, the solder bumps 132 and 134, the vias 136, and the solder bumps 146 and 162, to circuitry and/or traces in the PCB 160. FIG. 3 further illustrates underfill 366 that has been deposited all along or along substantially all (e.g., 95%, 90%, 85%, 80%, 75%) of the interface between the ultrasound-on-a-chip 100 and the interposer 106 and encapsulates the solder bumps 146 and 162. The underfill 366 may help improve the mechanical and thermal properties of the solder bonds between the ultrasound-on-a-chip 100 and the interposer 106.

It should be appreciated that in some embodiments, the interposer 106 may be coupled to the ultrasound-on-a-chip 100 prior to the interposer 106 being coupled to the PCB 160.

FIG. 4 illustrates a cross-sectional view of another example ultrasound device, in accordance with certain embodiments described herein. The ultrasound device of FIG. 4 differs from the ultrasound device of FIG. 3 in that the underfill 366 only encapsulates the solder bumps 146 and 162, and the rest of the interface between the ultrasound-on-a-chip 100 and the interposer 106 is empty. In some embodiments, substantially all (e.g., 95%, 90%, 85%, 80%, 75%, etc.) of the rest of the interface between the ultrasound-on-a-chip 100 and the interposer 106 may be empty. In some embodiments, a portion of the interface between the ultrasound-on-a-chip 100 and the interposer 106 may be empty.

FIG. 5 illustrates a cross-sectional view of another example ultrasound device, in accordance with certain embodiments described herein. The ultrasound device of FIG. 5 differs from the ultrasound device of FIG. 3 in that the underfill 366 only encapsulates the solder bumps 146 and 162, and an adhesive 568 is deposited along the rest of the interface between the ultrasound-on-a-chip 100 and the interposer 106. In some embodiments, the adhesive 568 may be deposited along substantially all (e.g., 95%, 90%, 85%, 80%, 75%, etc.) of the rest of the interface between the ultrasound-on-a-chip 100 and the interposer 106. In some embodiments, the adhesive 568 may be deposited along a portion of the interface between the ultrasound-on-a-chip 100 and the interposer 106. The adhesive 568 may help to attenuate ultrasound waves that exit the ultrasound-on-a-chip device 100 and/or may help to conduct heat away from the ultrasound-on-a-chip device 100.

FIG. 6 illustrates a cross-sectional views of another example ultrasound device during packaging, in accordance with certain embodiments described herein. FIG. 6 illustrates the ultrasound-on-a-chip 100, an interposer 606, and the PCB 160. The interposer 606 includes a heat sink portion 640, vias 636, solder bumps 634, and solder bumps 646. The interposer 606 differs from the interposer 106 in that the interposer 606 includes an electrical connectivity portion 638. The interposer 606 may thus be considered a hybrid interposer, in that it includes the electrical connectivity portion 638 and the heat sink portion 640. The electrical connectivity portion 638 includes vias 636, solder bumps 634, and solder bumps 646. The electrical connectivity portion 638 may be made of organic, glass, or silicon material. For example, the electrical connectivity portion 638 may be formed using standard processes and materials (e.g., FR4 or BT) for forming printed circuit boards. The solder bumps 634 are on an upper face of the interposer 606 and the solder bumps 646 are on a lower face of the interposer 606. The vias 636 electrically connect the solder bumps 634 to the solder bumps 646. The heat sink portion 640 may be embedded in the electrical connectivity portion 638 and may include aluminum nitride, aluminum oxide, beryllium, and/or low-temperature co-fired ceramic (LTCC). In FIG. LLL, underfill 366 encapsulates the solder bumps 132 and 634 and is disposed all along the interface between the ultrasound-on-a-chip 100 and the interposer 606. However, in some embodiments, the underfill 366 may only encapsulate the solder bumps 132 and 634, and other regions of the interface may be empty (as in FIG. 4) or there may be adhesive 568 disposed along these regions of the interface (as in FIG. 5).

FIG. 7 illustrates a cross-sectional view of another example ultrasound device during packaging, in accordance with certain embodiments described herein. FIG. 7 illustrates the ultrasound-on-a-chip 100, an interposer 706, and the PCB 160. The interposer 706 includes a heat sink portion 740, vias 736, solder bumps 734, and solder bumps 746. The interposer 706 differs from the interposer 106 in that the interposer 706 includes a copper patterns 790, copper patterns 794, and vias 792. The copper patterns 790 may be patterns of copper plated on the top surface of the interposer 706. The copper patterns 794 may be patterns of copper plated on the top surface of the interposer 706. The vias 736 pass through the interposer 706 and connect the copper patterns 790 to the copper patterns 794. The copper patterns 790 may protrude upwards towards the ultrasound-on-a-chip 100, and due to their proximity to the ultrasound-on-a-chip 100 help to improve conduction of heat away from the ultrasound-on-a-chip 100. For example, if the height of bonded solder bumps 132 and 734 is 50 microns, the copper patterns 790 may have a height of 25 microns, thereby reducing the gap between the ultrasound-on-a-chip 100 and the interposer 706 in certain regions. The copper patterns 790, copper patterns 794, and vias 792 may also help to strengthen the heat sink portion 740 of the interposer 706. It may be helpful for the copper patterns 790 not to touch the ultrasound-on-a-chip 100 to reduce reflection of ultrasound waves back to the ultrasound-on-a-chip 100. The interposer 706 may be considered a direct-plated copper (DPC) interposer 706. It should be appreciated that the copper patterns 790, copper patterns 794, and vias 792 may be used in any of the interposers or heat sinks described herein. It should also be appreciated that the interposer 706 may include more copper patterns 790, copper patterns 794, and vias 792 than shown.

FIGS. 1-7 illustrate an ultrasound-on-a-chip that includes TSVs. Electrical signals may be transmitted from the ultrasound-on-a-chip, through the TSVs, through vias in an interposer coupled to the ultrasound-on-a-chip, and to a PCB. TSVs in the ultrasound-on-a-chip device may be helpful for the following reasons:

1. Compared with other interconnect for electrically connecting the ultrasound-on-a-chip to the external environment that may require longer electrical paths, TSVs may present lower parasitic inductance and resistance, leading to higher power efficiency and less heating of the ultrasound device.

2. Using TSVs may facilitate using a surface mount technology (SMT) process for coupling the ultrasound-on-a-chip to an interposer. It may be possible to solder bond most or all of the solder bumps of the interposer to the solder bumps of the ultrasound-on-a-chip at once, and it may be possible to use a single machine to solder bond multiple ultrasound-on-a-chips to multiple interposers at once. In other words, using TSVs may facilitate a high throughput packaging process that may be better suited for packaging high volumes of ultrasound-on-a-chips.

3. During ultrasound imaging, the upper face of the ultrasound-on-a-chip may be pressed against a subject. (It should be noted that one or more structures, such as an acoustic lens, may be disposed between the upper face of the ultrasound-on-a-chip and the subject during imaging.) The TSVs are not disposed near the upper face of the ultrasound-on-a-chip and accordingly may be less subject to damage due to this pressure.

4. Other interconnect structures for electrically connecting to the ultrasound-on-a-chip may extend laterally from the upper face of the ultrasound-on-a-chip. Accordingly, the upper face of the packaged ultrasound-on-a-chip may be larger in size than the upper face of the ultrasound-on-a-chip itself due to this lateral extension. (To measure these sizes, one may look downwards from a bird's-eye view at the packaged ultrasound-on-a-chip. The size of the upper face of the packaged ultrasound-on-a-chip may be the total area of the packaged ultrasound-on-a-chip visible from a bird's-eye view when looking downwards at the ultrasound-on-a-chip. The size of the upper face of the ultrasound-on-a-chip may be the area of just the ultrasound-on-a-chip visible from a bird's-eye view when looking downwards at the ultrasound-on-a-chip, excluding any interconnect or other packaging.) As discussed above, TSVs are not disposed near the upper face of the ultrasound-on-a-chip, and therefore do not contribute significantly to the size of the upper face of the ultrasound-on-a-chip. In some embodiments, the size of the upper face of the packaged ultrasound-on-a-chip may be approximately the same as the size of the upper face of the unpackaged ultrasound on a chip. (For example, the size of the upper face of the packaged ultrasound-on-a-chip may between or including 100%-101%, 100%-105%, 100%-110%, 100%-120%, 100%-125%, 100%-130%, 100%-140%, or 100%-150% of the size of the upper face of the unpackaged ultrasound-on-a-chip).

Avoiding increasing the size of the upper face of the packaged ultrasound-on-a-chip with interconnects may help to reduce the overall size of the ultrasound device and enable form factors for the ultrasound device such as ultrasound patches. Additionally, avoiding increasing the size of the upper face of the packaged ultrasound-on-a-chip with interconnect may, for example, help the upper face of the packaged ultrasound-on-a-chip fit between a subject's ribs during imaging. This may be especially helpful for cardiac imaging. Additionally, avoiding increasing the size of the upper face of the packaged ultrasound-on-a-chip with interconnect may help to reduce the amount of acoustic lens material that is deposited on the upper face of the packaged ultrasound-on-a-chip. In particular, reducing the thickness of the acoustic lens material may help to reduce attenuation of pressure waves generated by the ultrasound device.

In any of the interposers or heat sinks described herein, an outer portion of the interposer may be thicker than an inner portion, forming a recess. For example, in some embodiments, the electrical connectivity portion 638 of the interposer 606 may be thicker than the heat sink portion 640. The recess may be empty or may be filled with underfill or adhesive, for example, at the interface between the ultrasound-on-a-chip and the interposer.

FIGS. 8-11 illustrate cross-sectional views of another example ultrasound device during packaging, in accordance with certain embodiments described herein. FIG. 8 includes an ultrasound-on-a-chip 800, an interposer 806, adhesive 868, and the PCB 160. The ultrasound-on-a-chip 800 differs from the ultrasound-on-a-chip 100 in that the ultrasound-on-a-chip 800 includes bond pads 872 on its upper face and lacks the TSVs 128. The bond pads 872 may be electrically connected to circuitry and/or interconnect within the ultrasound-on-a-chip 800 (not visible in FIG. 8). The interposer 806 includes a heat sink portion 840, vias 836, and solder bumps 846 on its lower face. The interposer 806 differs from the interposer 106 in that the interposer 806 lacks solder bumps on the top face of the interposer 806 and further includes bond pads 878 on the top face of the interposer 806. The vias 836 electrically connect the bond pads 878 to the solder bumps 846.

In FIG. 9, the interposer 806 and the PCB 160 are coupled together. The interposer 806 may be bonded to the PCB 160 using a surface-mount technology (SMT) process. In particular, the solder bumps 846 on the lower surface of the interposer 806 may be solder bonded to the solder bumps 162 on the upper surface of the PCB 160. FIG. 8 further illustrates underfill 264 that has been deposited between the interposer 806 and the PCB 160. The underfill 264 may help improve the mechanical and thermal properties of the solder bonds between the interposer 806 and the PCB 160.

In FIG. 10, the ultrasound-on-a-chip 800 and the interposer 806 are coupled together. The ultrasound-on-a-chip 800 is adhered to the interposer 806 through the adhesive 868. It should be appreciated that in some embodiments, the interposer 806 may be coupled to the ultrasound-on-a-chip 800 before the interposer 806 is coupled to the PCB 160.

Figure 11:
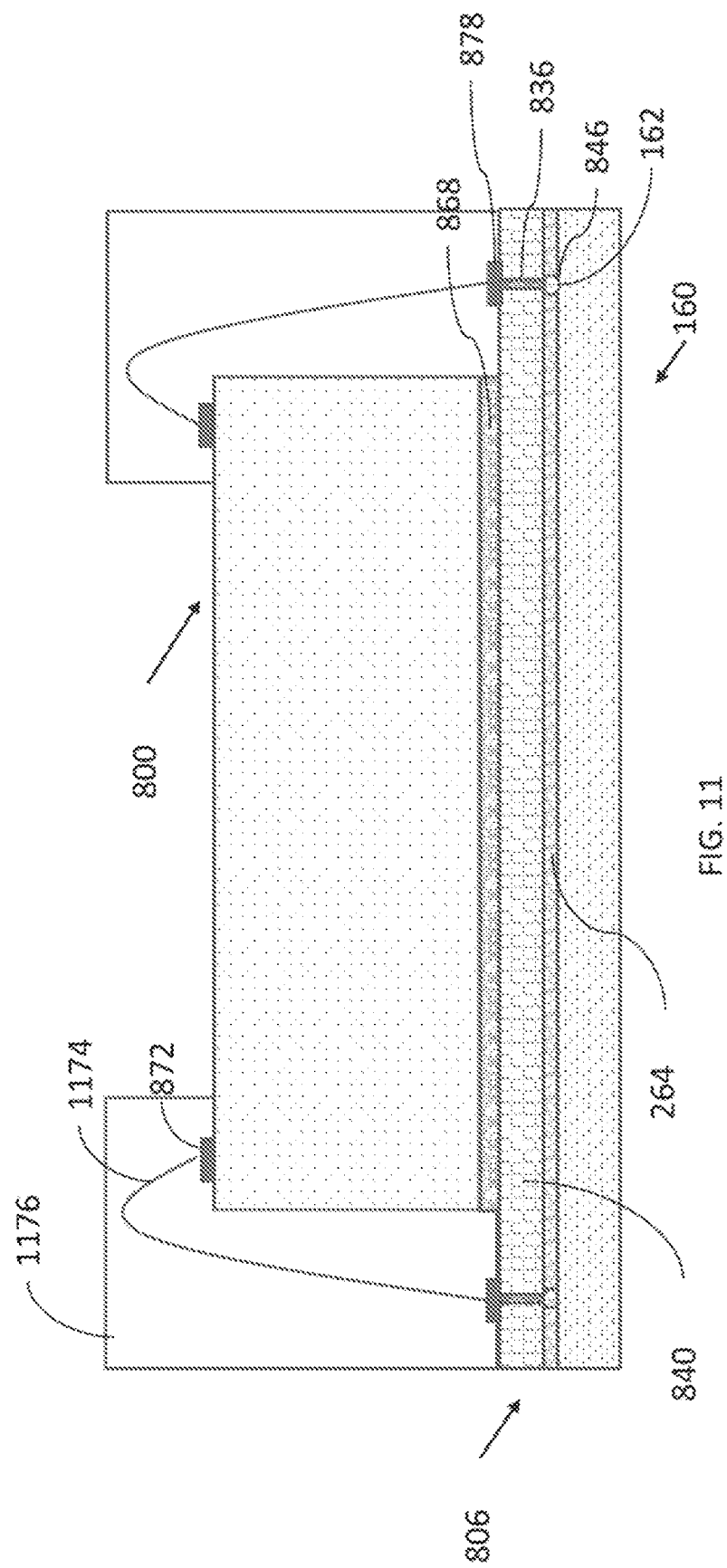
FIG. 11 illustrates another cross-sectional view of the example ultrasound device of FIG. 8 during packaging, in accordance with certain embodiments described herein.

In FIG. 11, the ultrasound-on-a-chip 800 is wirebonded to the interposer 806. FIG. 11 includes wirebonds 1174 and encapsulation 1176. The wirebonds 1174 extend between the bond pads 872 on the ultrasound-on-a-chip 800 and the bond pads 878 on the interposer 806. Thus, circuitry and/or interconnect in the ultrasound-on-a-chip 800 may be electrically connected to circuitry and/or traces within the PCB 160 through the bond pads 872, wirebonds 1174, bond pads 878, vias 836, and solder bumps 846 and 162. The encapsulation 1176 encapsulates the wirebonds 1174 and may serve to protect and insulate the wirebonds 1174. It should be appreciated that there may be more wirebonds 1174 than shown.

When the wirebonds 1174 extend from the ultrasound-on-a-chip 800 to the interposer 806, the wirebonds 1174 may be shorter than wirebonds extending from the ultrasound-on-a-chip 800 to the PCB 860. The shorter wirebonds 1174 may result in a smaller upper face of the packaged ultrasound-on-a-chip 800, which may help to reduce the overall size of the ultrasound device, may help the upper face of the packaged ultrasound-on-a-chip 800 fit between a subject's ribs during imaging, and may help to reduce the amount of acoustic lens material that is deposited on the upper face of the packaged ultrasound-on-a-chip 800.

Figure 12:
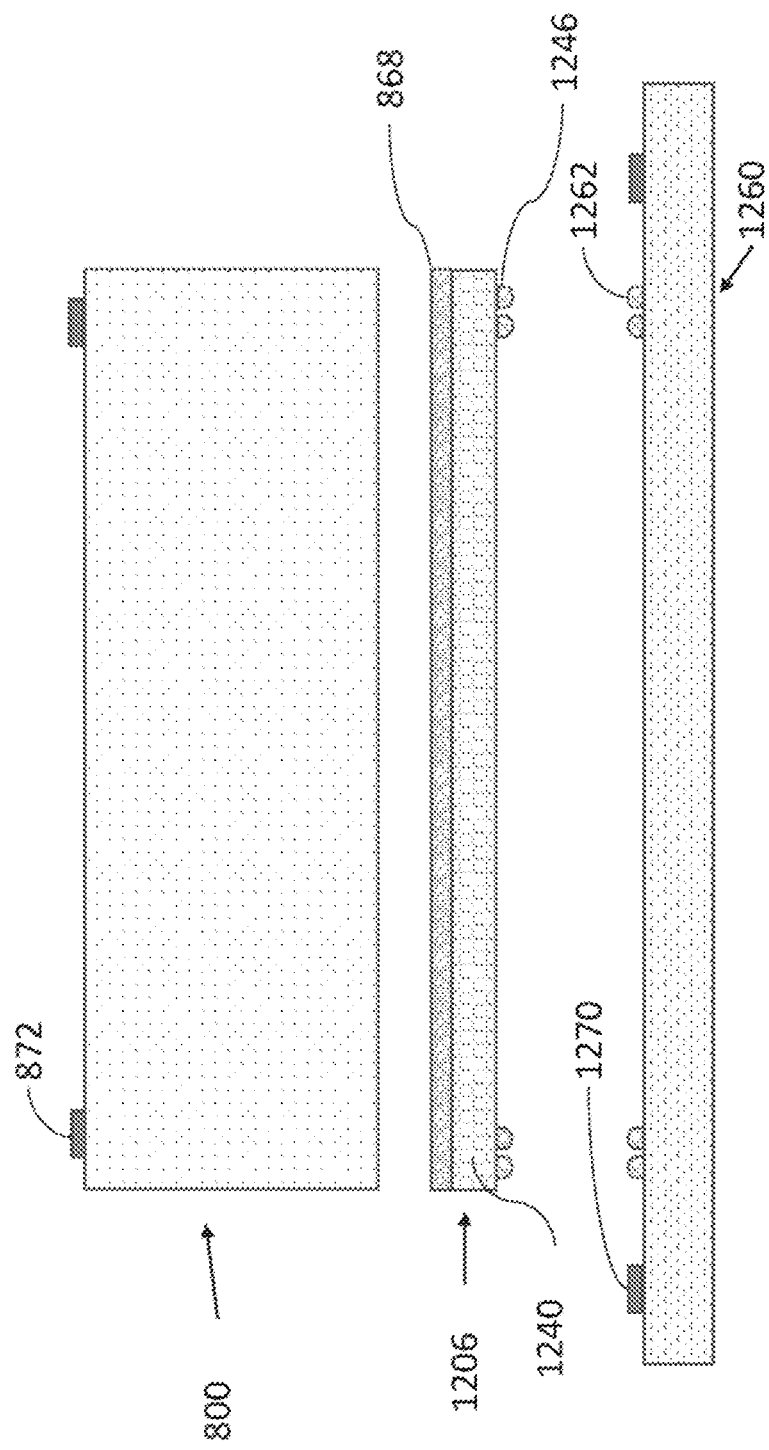
FIG. 12 illustrates a cross-sectional view of an example ultrasound device during packaging, in accordance with certain embodiments described herein.

FIGS. 12-15 illustrate cross-sectional views of another example ultrasound device during packaging, in accordance with certain embodiments described herein. FIG. 12 includes an ultrasound-on-a-chip 800, a heat sink 1206, adhesive 868, and a PCB 1260. The heat sink 1206 includes a heat sink portion 1240 and solder bumps 1246 on its lower face. The heat sink 1206 differs from the interposer 806 in that the heat sink 1206 lacks the vias 836 and the bond pads 878 on the top face of the heat sink 1206. The PCB 1260 includes solder bumps 1262 on its upper face. The PCB 1260 differs from the PCB 160 in that the PCB 1260 includes bond pads 1270 on its upper face. The bond pads 1270 may be electrically connected to circuitry and/or traces within the PCB 1260 (not visible in FIG. 12).

Figure 13:
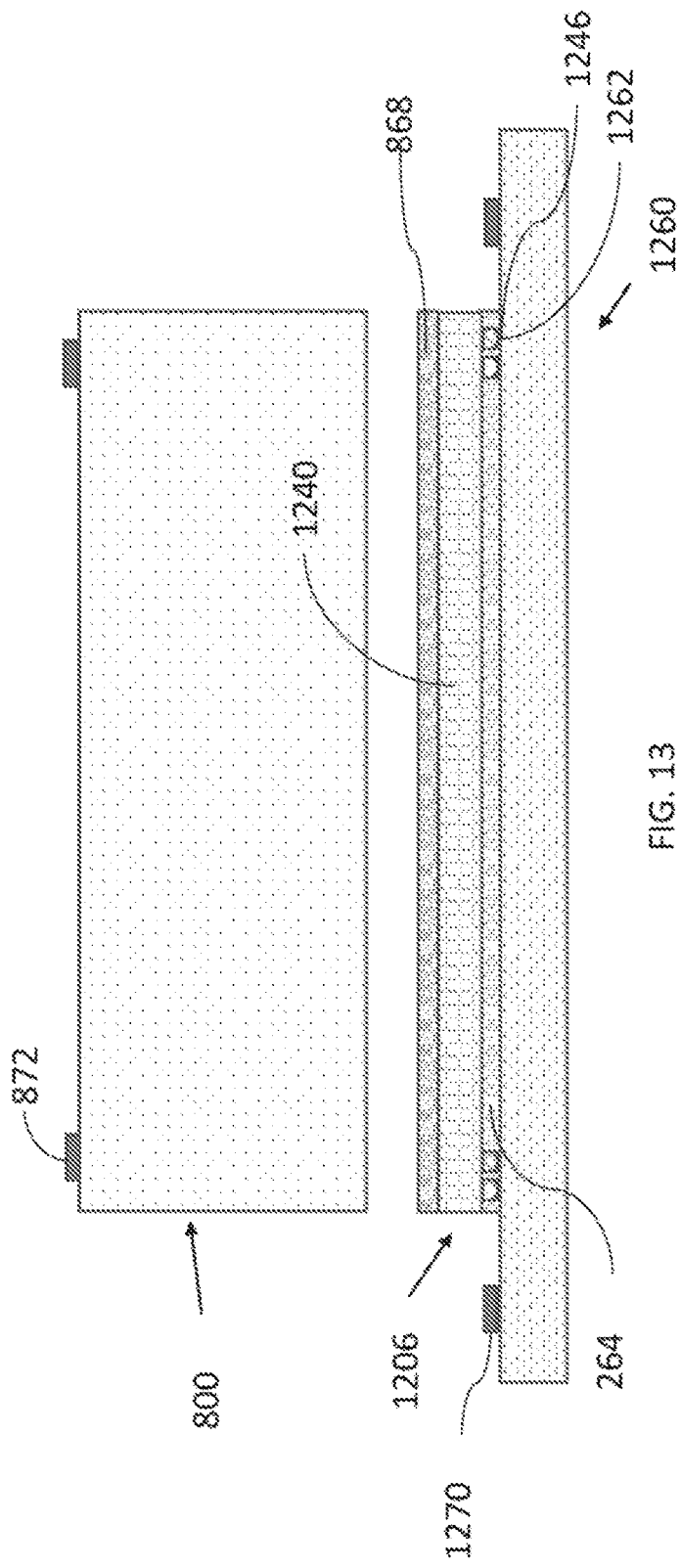
FIG. 13 illustrates another cross-sectional view of the example ultrasound device of FIG. 12 during packaging, in accordance with certain embodiments described herein.

In FIG. 13, the heat sink 1206 and the PCB 1260 are coupled together. The heat sink 1206 may be bonded to the PCB 1260 using a surface-mount technology (SMT) process. In particular, the solder bumps 1246 on the lower surface of the heat sink 1206 may be solder bonded to the solder bumps 1262 on the upper surface of the PCB 1260. FIG. 13 further illustrates underfill 264 that has been deposited between the heat sink 1206 and the PCB 1260. The underfill 264 may help improve the mechanical and thermal properties of the solder bonds between the heat sink 1206 and the PCB 1260.

Figure 14:
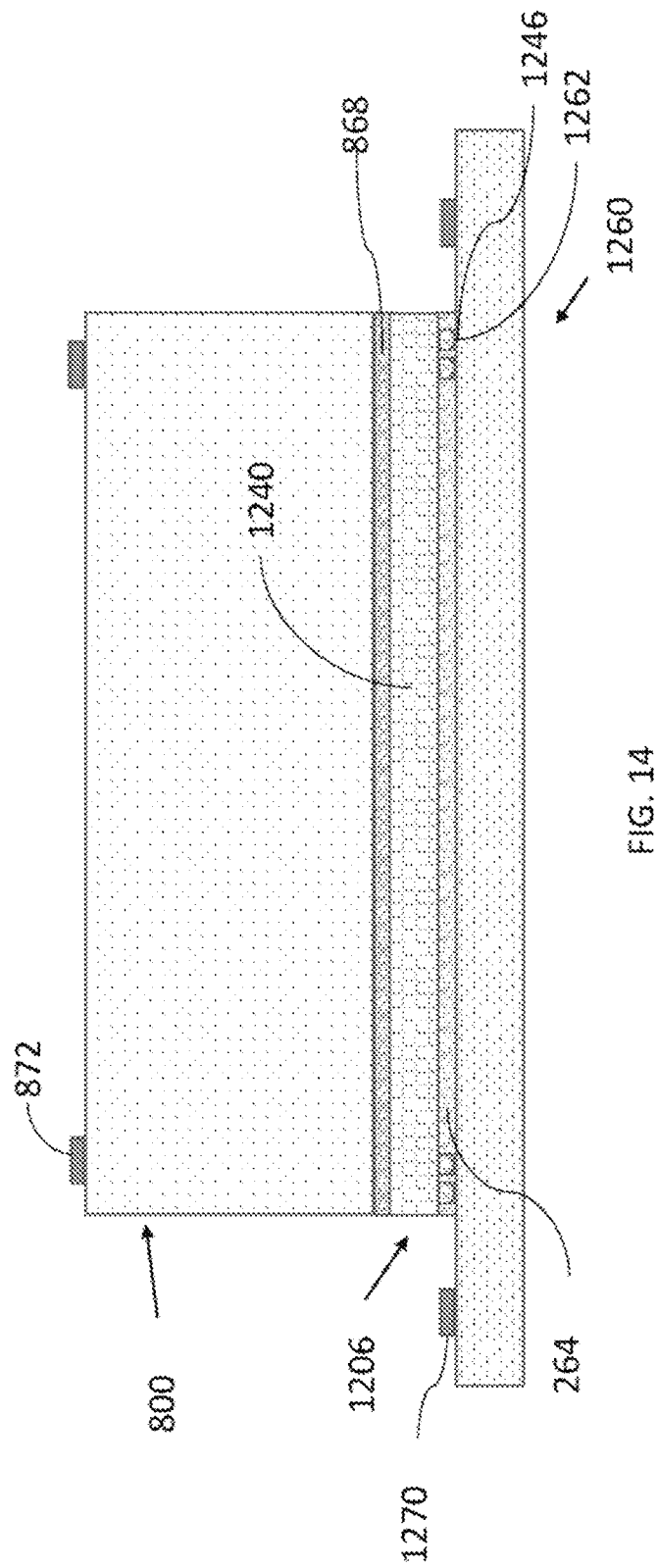
FIG. 14 illustrates another cross-sectional view of the example ultrasound device of FIG. 12 during packaging, in accordance with certain embodiments described herein.

In FIG. 14, the ultrasound-on-a-chip 800 and the heat sink 1206 are coupled together, in accordance with certain embodiments described herein. The ultrasound-on-a-chip 800 is adhered to the heat sink 1206 through the adhesive 868. It should be appreciated that in some embodiments, the heat sink 1206 may be coupled to the ultrasound-on-a-chip 800 before the interposer 806 is coupled to the PCB 1260.

Figure 15:
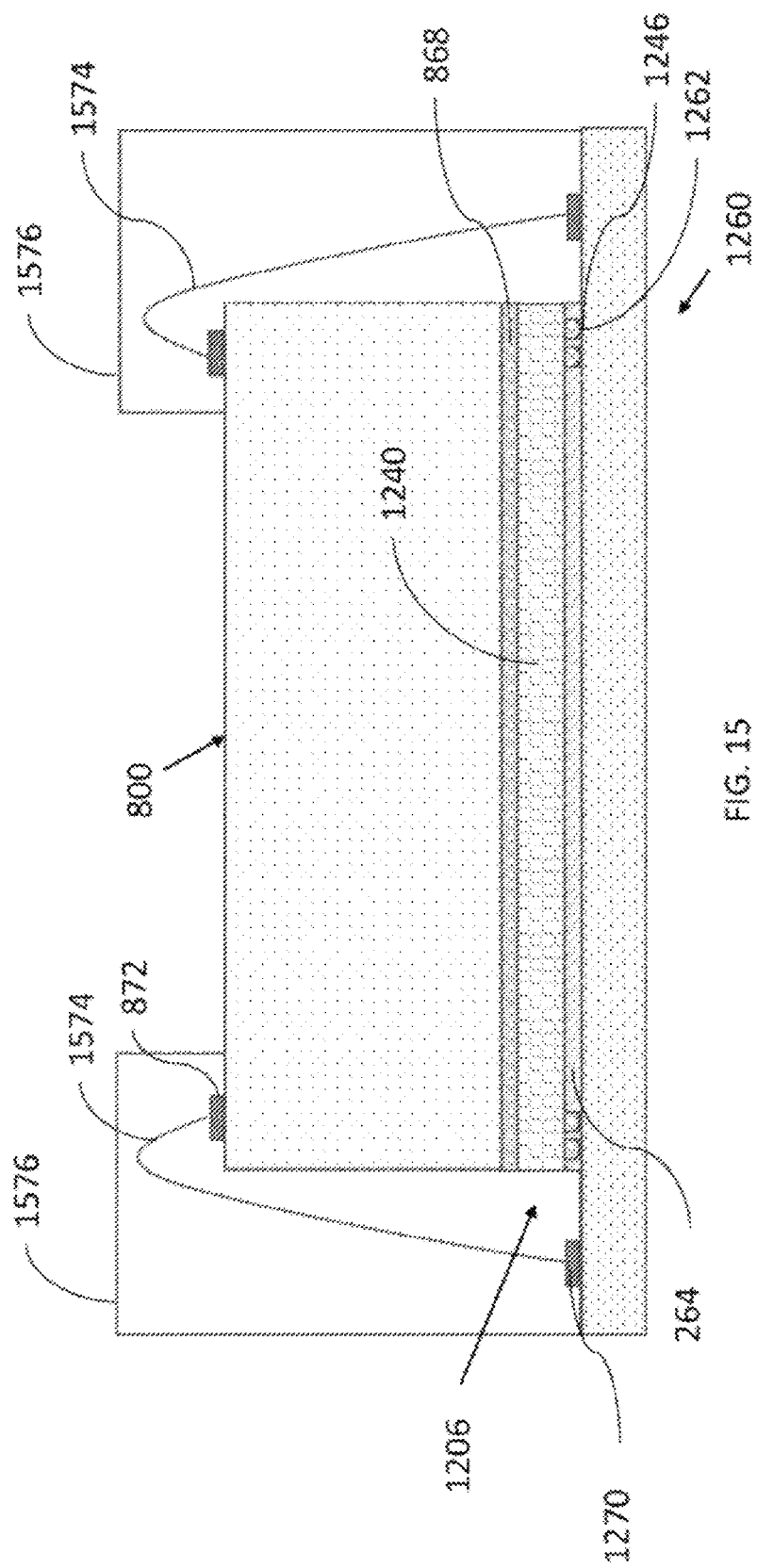
FIG. 15 illustrates another cross-sectional view of the example ultrasound device of FIG. 12 during packaging, in accordance with certain embodiments described herein.

In FIG. 15, the ultrasound-on-a-chip 800 is wirebonded to the PCB 1260. FIG. 15 includes wirebonds 1574 and encapsulation 1576. The wirebonds 1574 extend between the bond pads 872 on the ultrasound-on-a-chip 800 and the bond pads 1270 on the PCB 1260. Thus, circuitry and/or interconnect in the ultrasound-on-a-chip 800 may be electrically connected to circuitry and/or traces within the PCB 1260 through the bond pads 872, wirebonds 1574, and bond pads 1270. The encapsulation 1576 encapsulates the wirebonds 1574 and may serve to protect and insulate the wirebonds 1574. It should be appreciated that there may be more wirebonds 1574 than shown.

As can be seen in FIGS. 12-15, when the wirebonds 1574 extend from the ultrasound-on-a-chip 800 to the PCB 1260, the heat sink 1266 may not include vias as other interposers described herein do.

Figure 16:
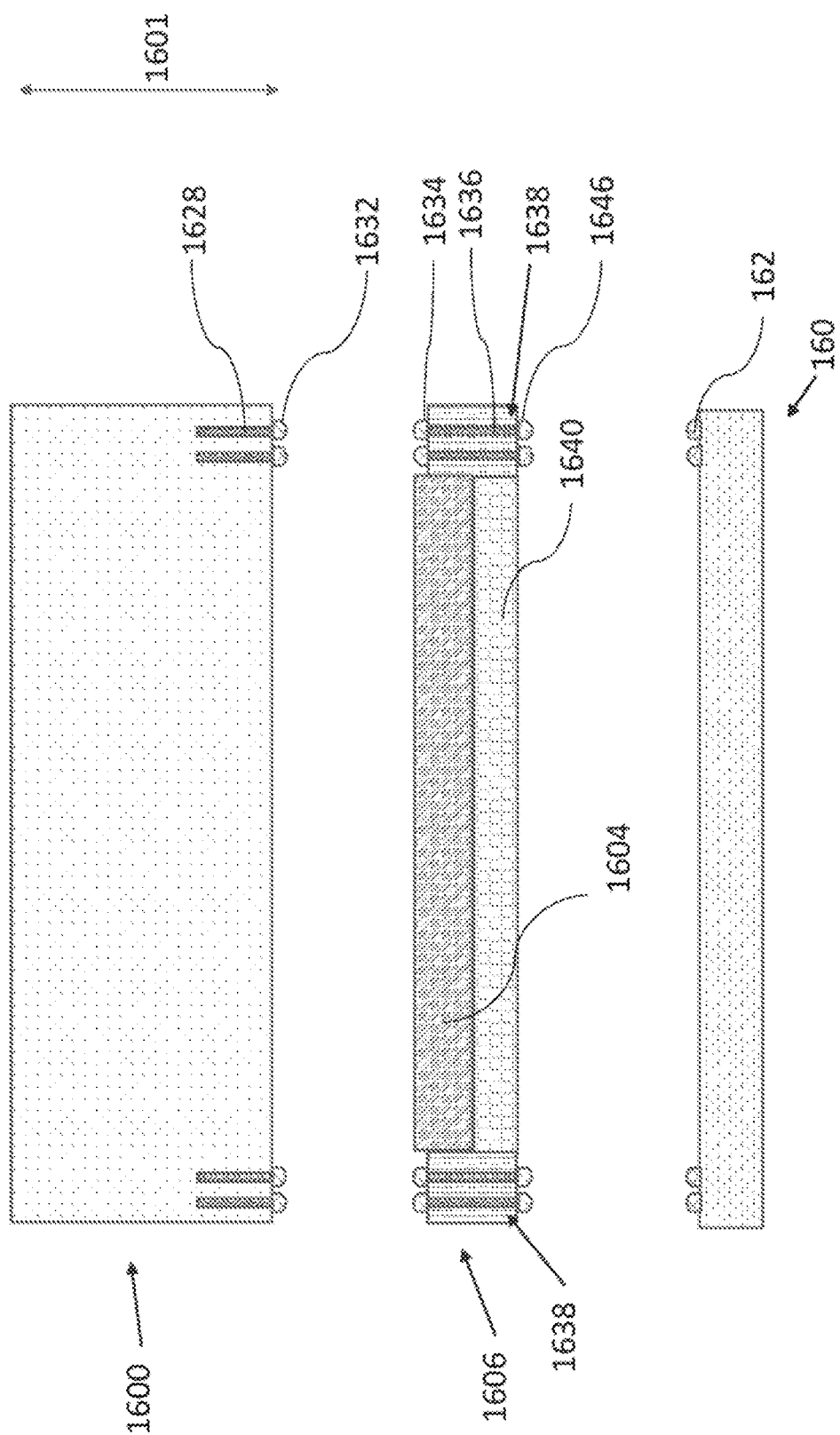
FIG. 16 illustrates a cross-sectional view of an example ultrasound device during packaging, in accordance with certain embodiments described herein.
Figure 17:
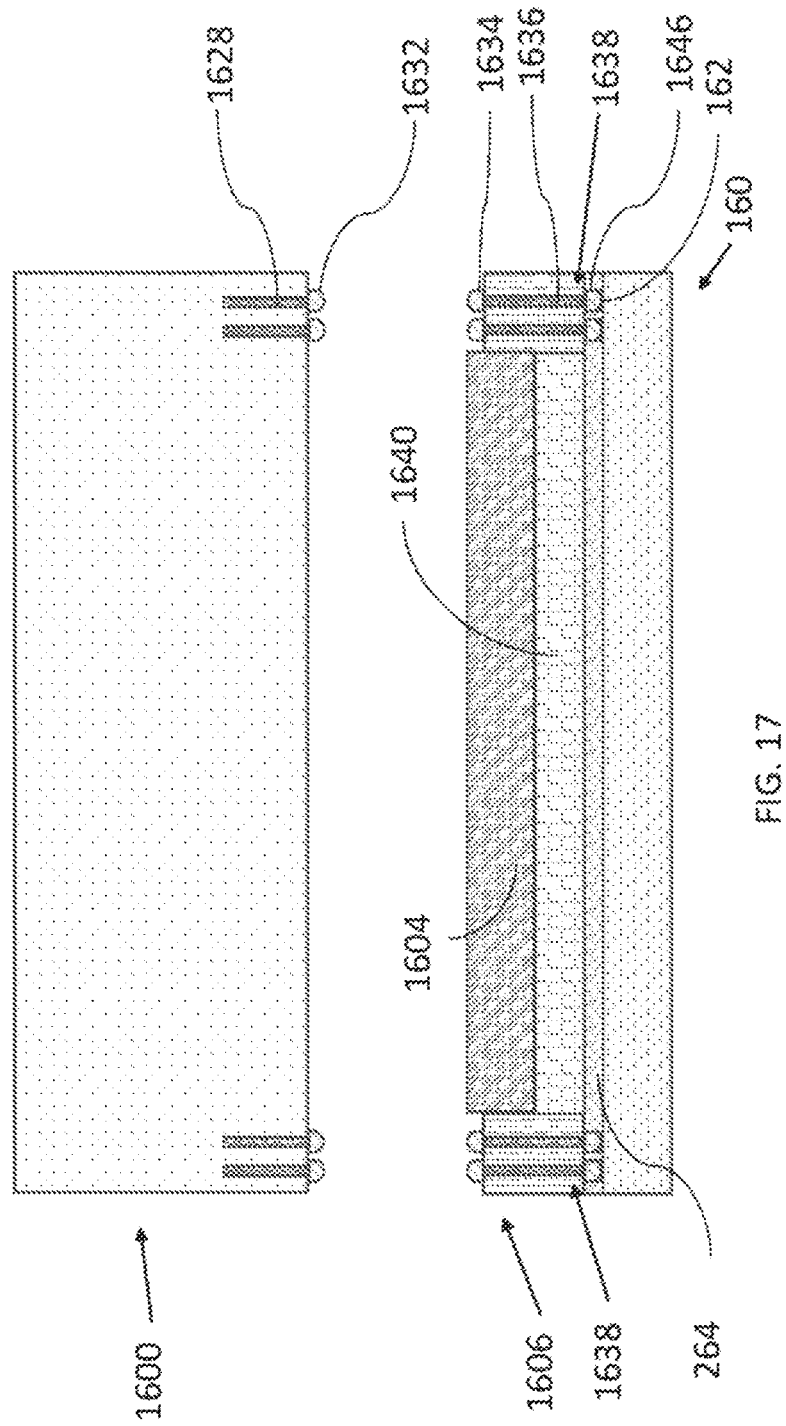
FIG. 17 illustrates another cross-sectional view of the example ultrasound device of FIG. 16 during packaging, in accordance with certain embodiments described herein.
Figure 18:
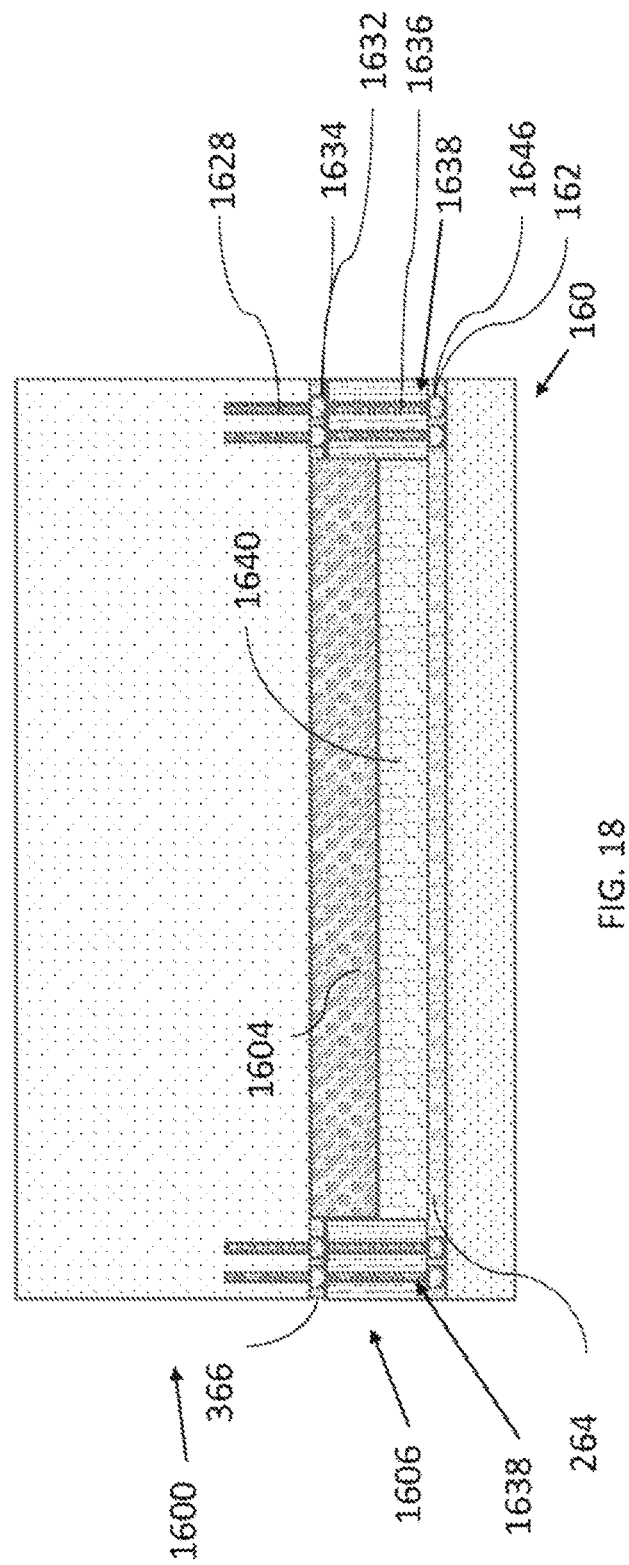
FIG. 18 illustrates another cross-sectional view of the example ultrasound device of FIG. 16 during packaging, in accordance with certain embodiments described herein.

FIGS. 16-18 illustrate cross-sectional views of another example of an ultrasound device during packaging, in accordance with certain embodiments described herein. FIG. 16 illustrates an ultrasound-on-a-chip 1600, an interposer 1606, and the printed circuit board (PCB) 160.

The ultrasound-on-a-chip 1600 includes through-silicon vias (TSVs) 1628 and solder bumps 1632. The ultrasound-on-a-chip 1600 differs from the ultrasound-on-a-chip 100 in that the height 1601 of the ultrasound-on-a-chip 1600 is not reduced after it is fabricated, prior to packaging. Thus, the height of the ultrasound-on-a-chip 1600 may be between or equal to approximately 760-800 microns.

The interposer 1606 includes a heat sink portion 1640, an electrical connectivity portion 1638, vias 1636, solder bumps 1634, and solder bumps 1646. The interposer 1606 differs from the interposer 606 in that the electrical connectivity portion 1638 is thicker than the heat sink portion 1640, forming a recess for the backing material 1604.

The backing material 1604 is coupled to the upper face of the interposer 1606. However, in some embodiments, the backing material 1604 may be coupled to the lower face of the ultrasound-on-a-chip 1600. In some embodiments, the thickness of the backing material 1604 may be between or equal to approximately 400-600 microns. In some embodiments, the backing material 1604 may include an epoxy containing tungsten. In some embodiments, the epoxy may be a two-stage epoxy, and a first cure stage may be performed to couple the backing material 1604 to the interposer 1606, and a second cure stage may be performed to couple the ultrasound-on-a-chip 1600 to the backing material 1604. In some embodiments, the backing material 1604 may be screen-printed onto the interposer 1606 when the upper face of the interposer 1606 is facing upwards such that gravity causes the backing material 1604 to settle onto the interposer 1606. In some embodiments, the backing material 1604 may be coupled to the lower face of the ultrasound-on-a-chip 1600, and the backing material 1604 may be screen-printed onto the ultrasound-on-a-chip 1600 when the lower face of the interposer 1606 is facing upwards such that gravity causes the backing material 1604 to settle onto the ultrasound-on-a-chip 1600.

As described above, the height of the ultrasound-on-a-chip 1600 is not reduced after it is fabricated (e.g., using grinding or etching). Thus, the height of the ultrasound-on-a-chip 1600 may be between or equal to approximately 760-800 microns. The backing material 1604 at the interface between the ultrasound-on-a-chip 1600 and the interposer 1606 may serve an acoustic matching function and force long-wavelength components of ultrasound waves to exit the ultrasound-on-a-chip through the backing material 1604 and be attenuated in the backing material 1604, thus reducing spurious acoustic reflections back into the ultrasound-on-a-chip 1600 and interference. Maintaining the height of the ultrasound-on-a-chip 1600 (rather than thinning it) may be helpful for handling the ultrasound device during packaging.

In some embodiments, because the backing material 1604 is disposed between the ultrasound-on-a-chip 1600 and the interposer 1606, the height of the interposer 1606 and therefore the height of the vias 1636 in the interposer 1606 may depend on the thickness of the backing material 1604. Longer vias 1636 may contribute to higher inductance and/or resistance of the electrical connection from the ultrasound-on-a-chip 1600 to the interposer 1606 and the PCB 160. Avoiding high inductance may be especially helpful in an ultrasound-on-a-chip 1600 due to the large spikes in current that may be required to generate ultrasound signals. In some embodiments, the choice of the thickness of the backing material 1604 may include trading off between acoustic attenuation, efficiency of heat conduction to the heat sink portion 1640 of the interposer 1606, and inductance. For example, in some embodiments acoustic attenuation may increase with increased thickness of the backing material 1604, efficiency of heat conduction to the heat sink portion 1640 of the interposer 1606 may decrease with increased thickness of the backing material 1604, and inductance and/or resistance may increase with increased thickness of the backing material 1604.

In FIG. 17, the interposer 1606 and the PCB 160 are coupled together. The interposer 1606 may be bonded to the PCB 160 using a surface-mount technology (SMT) process. In particular, the solder bumps 1646 on the lower surface of the interposer 1606 may be solder bonded to the solder bumps 162 on the upper surface of the PCB 160. Therefore, circuitry and/or traces in the PCB 160 may be electrically connected, through the solder bumps 162 and 1646 and the vias 1636 to the solder bumps 1634 on the upper surface of the interposer 1606. FIG. 17 further illustrates underfill 264 that has been deposited between the interposer 1606 and the PCB 160. The underfill 264 may help improve the mechanical and thermal properties of the solder bonds between the interposer 1606 and the PCB 160.

In FIG. 18, the ultrasound-on-a-chip 1600 and the interposer 1606 are coupled together. The ultrasound-on-a-chip 1600 may be bonded to the interposer 1806 using a surface-mount technology (SMT) process. In particular, the solder bumps 1634 on the upper surface of the interposer 1606 may be solder bonded to the solder bumps 1632 on the lower surface of the ultrasound-on-a-chip 1600. Therefore, integrated circuitry and/or interconnect in the ultrasound-on-a-chip 1600 may be electrically connected, through the TSVs 1628, the solder bumps 1632 and 1634, the vias 1636, and the solder bumps 1646 and 162, to circuitry and/or traces in the PCB 160. As described above, a second cure stage for the backing material 1604 may be performed to couple the ultrasound-on-a-chip 1600 to the backing material 1604 in the interposer 1606. FIG. 18 further illustrates underfill 366 that has been deposited between the ultrasound-on-a-chip 1600 and the interposer 1606 at the interface between the solder bumps 1634 and 1636. The underfill 366 may help improve the mechanical and thermal properties of the solder bonds between the ultrasound-on-a-chip 1600 and the interposer 1606. The backing material 1604 is disposed between the ultrasound-on-a-chip 1600 and the interposer 1606 at other portions of the interface. As can be seen, the ultrasound-on-a-chip 1600 sits on the heat sink portion 1640 of the interposer 1606 when the ultrasound-on-a-chip 1600 and the interposer 1606 are coupled together. In particular, substantially all (e.g., 100%, 99%, 95%, 90%, or 75%) of the lower surface of the backing material 1604 may be coupled to the heat sink portion 1640 of the interposer 1606 through thermally conductive adhesive when the ultrasound-on-a-chip 1600 and the interposer 1606 are coupled together. The interposer 1606 may be configured to contribute to establishing heat conduction from the ultrasound-on-a-chip 1600, through the backing material 1604, through the heat sink portion 1640, and out the bottom and sides of the packaged ultrasound-on-a-chip 1600. It should be appreciated that in some embodiments, the interposer 1606 may be coupled to the ultrasound-on-a-chip 1600 before the interposer 1606 is coupled to the PCB 160.

FIGS. 16-18 illustrate an ultrasound-on-a-chip device that includes TSVs. These TSVs may be helpful for the same reasons described above with reference to FIGS. 1-7.

Figure 19:
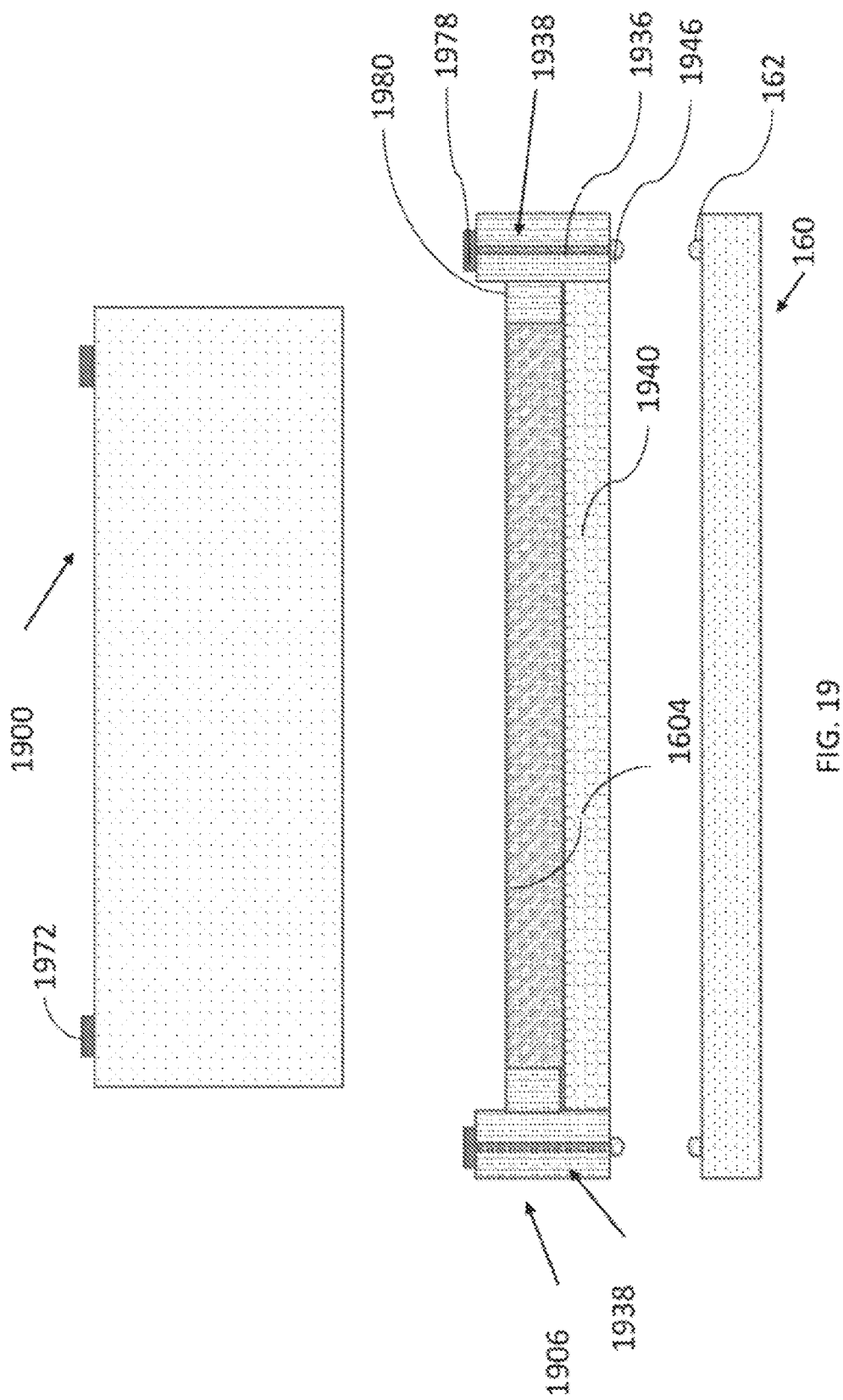
FIG. 19 illustrates a cross-sectional view of an example ultrasound device during packaging, in accordance with certain embodiments described herein.

FIGS. 19-22 illustrate cross-sectional views of another example ultrasound device during packaging, in accordance with certain embodiments described herein. FIG. 19 illustrates an ultrasound-on-a-chip 1900, an interposer 1906, the backing material 1604, and the PCB 160. The ultrasound-on-a-chip 1900 differs from the ultrasound-on-a-chip 1600 in that the ultrasound-on-a-chip 1900 includes bond pads 1972 on the upper face of the ultrasound-on-a-chip 1900 and lacks vias in the ultrasound-on-a-chip 1900 and solder bumps on the lower face of the ultrasound-on-a-chip 1900. The interposer 1906 includes an electrical connectivity portion 1938, a heat sink portion 1940, vias 1936, and solder bumps 1946 on the bottom face of the interposer 1906. The interposer 1906 differs from the interposer 1606 in that the interposer 1906 further includes a ledge 1980 extending inwards from the electrical connectivity portion 1938, includes bond pads 1978 on the upper face of the interposer 1906, and lacks solder bumps on the upper face of the interposer 1906. The vias 1936 electrically connect the bond pads 1978 to the solder bumps 1946.

Figure 20:
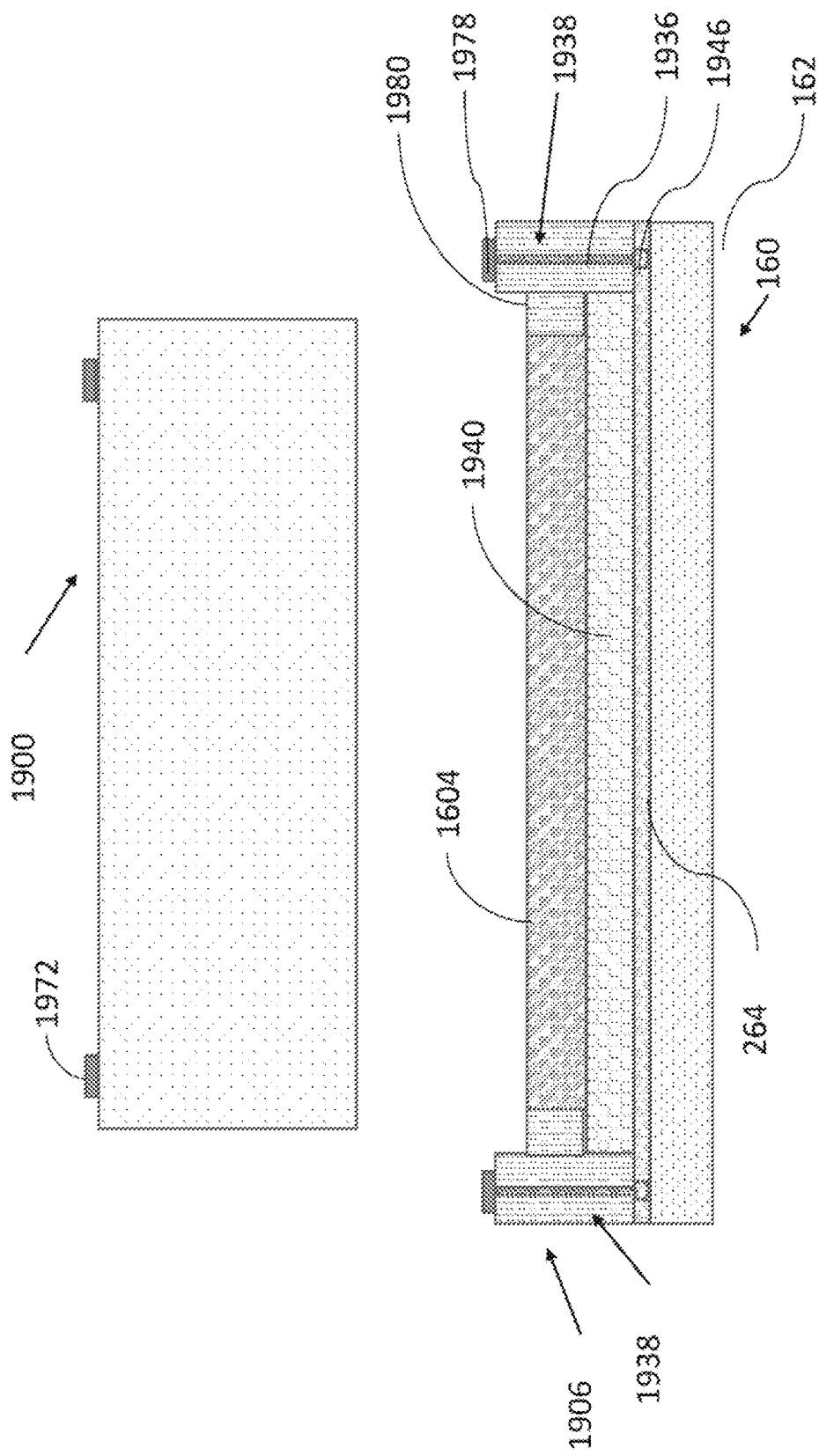
FIG. 20 illustrates another cross-sectional view of the example ultrasound device of FIG. 19 during packaging, in accordance with certain embodiments described herein.

In FIG. 20, the interposer 1906 and the PCB 160 are coupled together. The interposer 1906 may be bonded to the PCB 160 using a surface-mount technology (SMT) process. In particular, the solder bumps 1946 on the lower surface of the interposer 1906 may be solder bonded to the solder bumps 162 on the upper surface of the PCB 160. Therefore, circuitry and/or traces in the PCB 160 may be electrically connected, through the solder bumps 162 and 1946 and the vias 1936 to the bond pads 1978 on the upper surface of the interposer 1906. FIG. 20 further illustrates underfill 264 that has been deposited between the interposer 1906 and the PCB 160. The underfill 264 may help improve the mechanical and thermal properties of the solder bonds between the interposer 1906 and the PCB 160.

Figure 21:
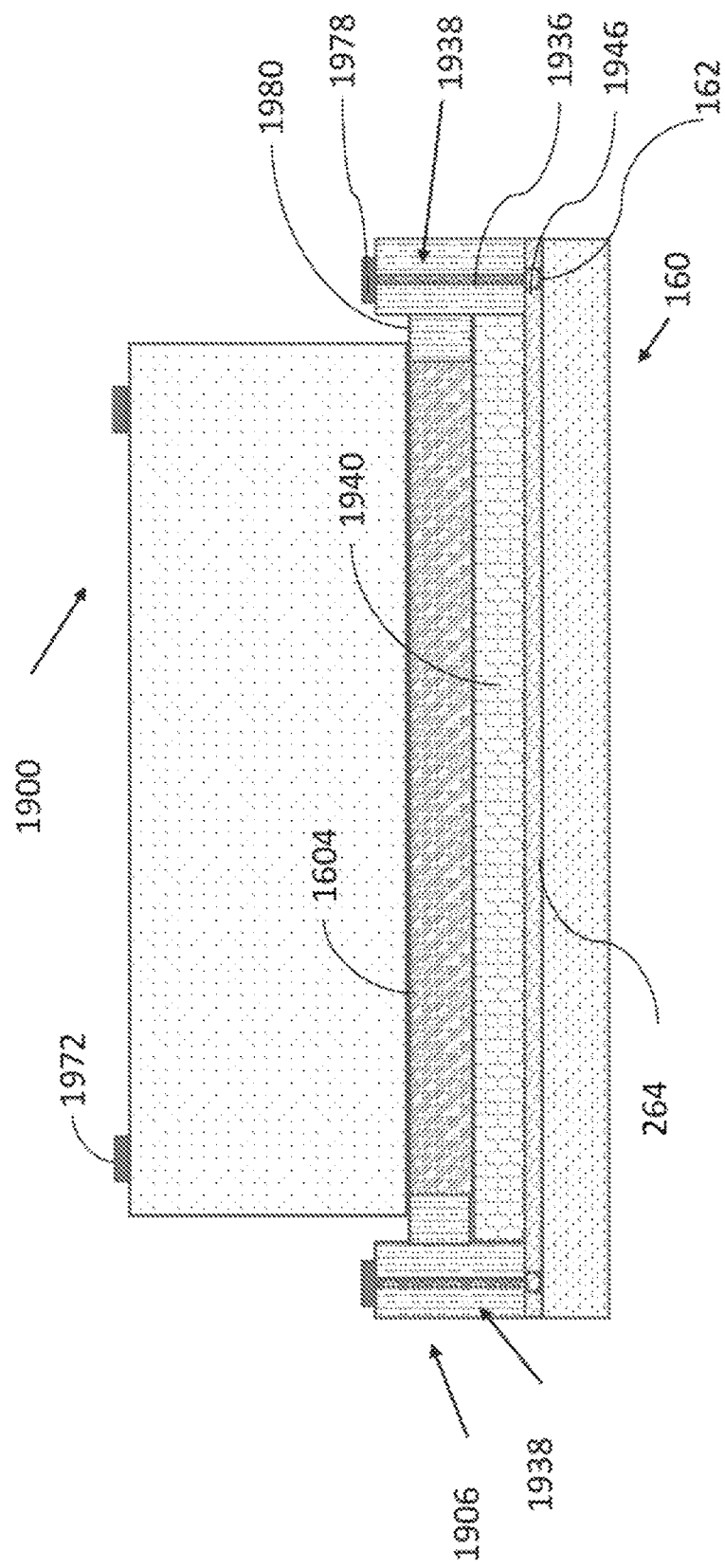
FIG. 21 illustrates another cross-sectional view of the example ultrasound device of FIG. 19 during packaging, in accordance with certain embodiments described herein.

In FIG. 21, the ultrasound-on-a-chip 1900 and the interposer 1906 are coupled together. The ultrasound-on-a-chip 1900 rests on the ledge 1980. In some embodiments, the ultrasound-on-a-chip 1900 may be coupled to adhesive on the ledge 1980. This may ensure structural integrity of the ultrasound device, in the absence of solder bonding between the ultrasound-on-a-chip 1900 and the interposer 1906. The ultrasound-on-a-chip 1900 may also be coupled to the backing material 1604. It should be appreciated that in some embodiments, the interposer 1906 may be coupled to the ultrasound-on-a-chip 1900 before the interposer 1906 is coupled to the PCB 160.

Figure 22:
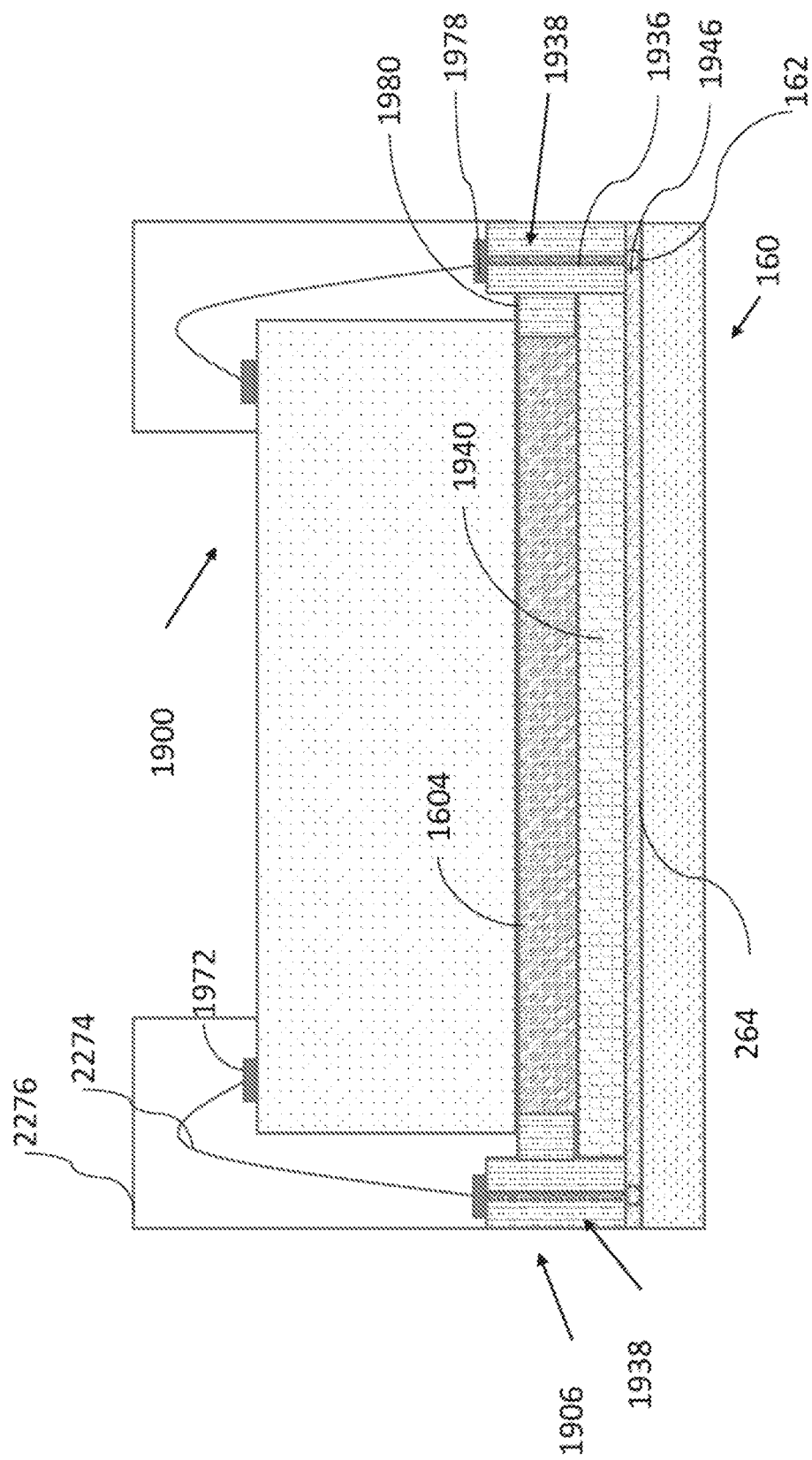
FIG. 22 illustrates another cross-sectional view of the example ultrasound device of FIG. 19 during packaging, in accordance with certain embodiments described herein.

In FIG. 22, the ultrasound-on-a-chip 1900 is wirebonded to the interposer 1906. FIG. 22 includes wirebonds 2274 and encapsulation 2276. The wirebonds 2274 extend between the bond pads 1972 on the ultrasound-on-a-chip 1900 and the bond pads 1978 on the interposer 1906. Thus, circuitry and/or interconnect in the ultrasound-on-a-chip 1900 may be electrically connected to circuitry and/or traces within the PCB 160 through the bond pads 1972, wirebonds 2274, bond pads 1978, vias 1936, and solder bumps 1946 and 162. The encapsulation 2276 encapsulates the wirebonds 2274 and may serve to protect and insulate the wirebonds 2274. It should be appreciated that there may be more wirebonds 2274 than shown.

Figure 23:
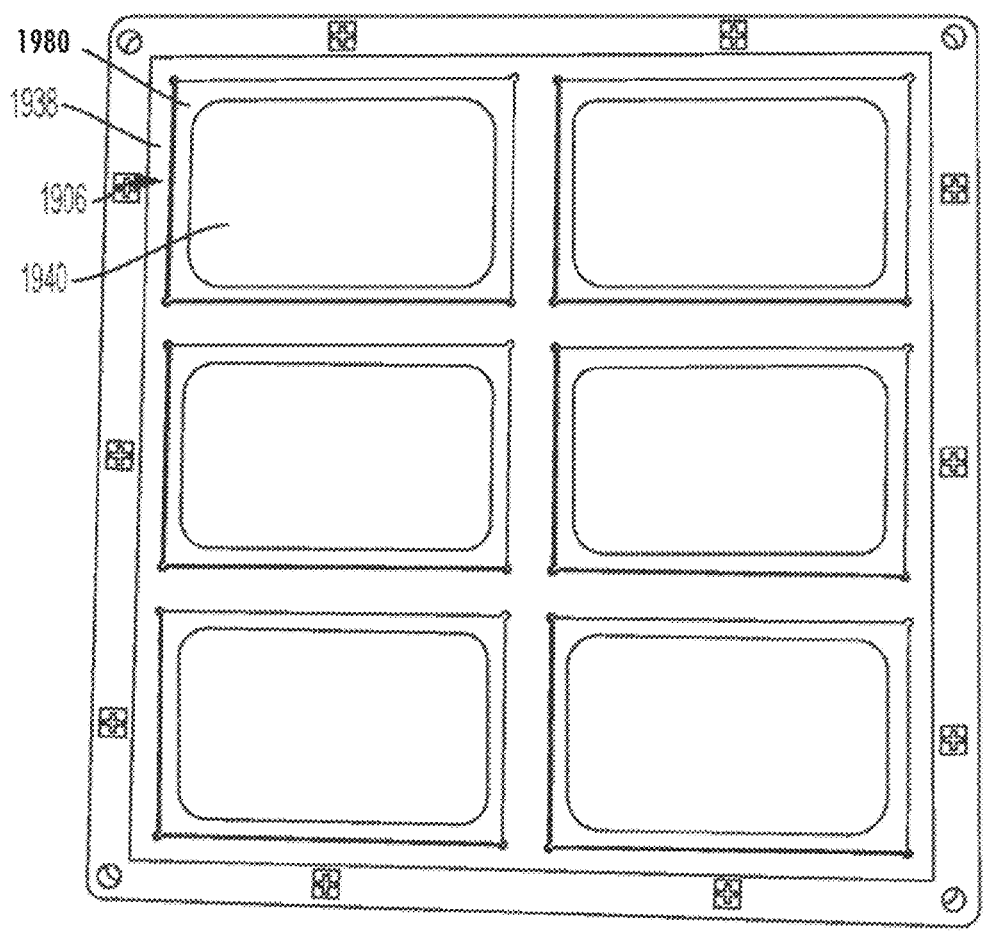
FIG. 23 illustrates an example bird's-eye view of the interposer of FIG. 19 in accordance with certain embodiments described herein.

FIG. 23 illustrates an example bird's-eye view of the interposer 1906 in accordance with certain embodiments described herein. In particular, FIG. 23 illustrates six hybrid interposers 1906, each including the electrical connectivity portion 1938, the heat sink portion 1940 (e.g., aluminum nitride, aluminum oxide, beryllium, and/or low-temperature co-fired ceramic (LTCC)), and the ledge 1980 extending inwards from the electrical connectivity portion 1938. To couple the ultrasound-on-a-chip 1900 to the interposer 1906, the ultrasound-on-a-chip 1900 may be lowered down onto the top face of the interposer 1906 visible in FIG. 23.

Figure 24:
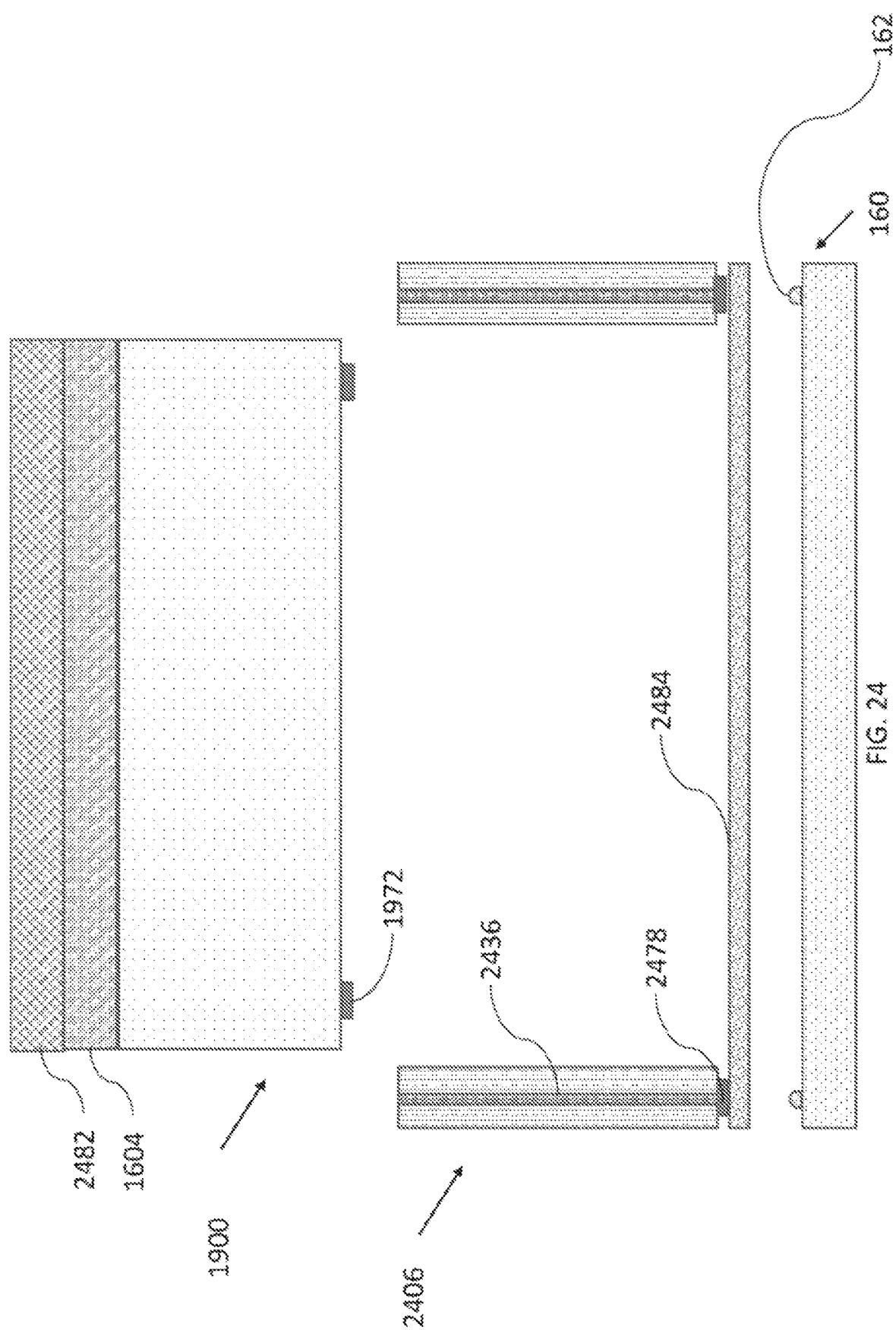
FIG. 24 illustrates a cross-sectional view of an example ultrasound device during packaging, in accordance with certain embodiments described herein.

FIGS. 24-28 illustrate cross-sectional views of another example ultrasound device, in accordance with certain embodiments described herein. FIG. 24 illustrates the ultrasound-on-a-chip 1900, backing material 1604, a heat sink 2482, an interposer 2406, a liner 2484, and the PCB 160. The ultrasound-on-a-chip 1900 is shown flipped in the vertical direction from the orientation in FIG. 19. The backing material 1604 is coupled to the ultrasound-on-a-chip 1900 (e.g., through adhesive not visible in FIG. 24) and the heat sink 2482 is coupled to the backing material 1604 (e.g., through adhesive not visible in FIG. 24). The heat sink 2482 may include ceramic material, such as aluminum nitride, aluminum oxide, beryllium, and/or low-temperature co-fired ceramic (LTCC). The interposer 2406 includes vias 2436 and bond pads 2478. The vias 2436 are electrically connected to the bond pads 2478. The interposer 2406 may be made of organic, glass, or silicon material. The liner 2484 may protect the bond pads 2478. The liner 2484 may be a residue-free removable liner and may include, for example, a polyimide tape, film, or sheet. In some embodiments, the liner 2484 may be electrostatic-discharge dissipative. While the interposer 2406 appears as two unconnected portions in FIG. 24, other portions of the interposer 2406 not visible in FIG. 24 may connect these two portions together. In some embodiments, the interposer 2406 may resemble a picture frame.

Figure 25:
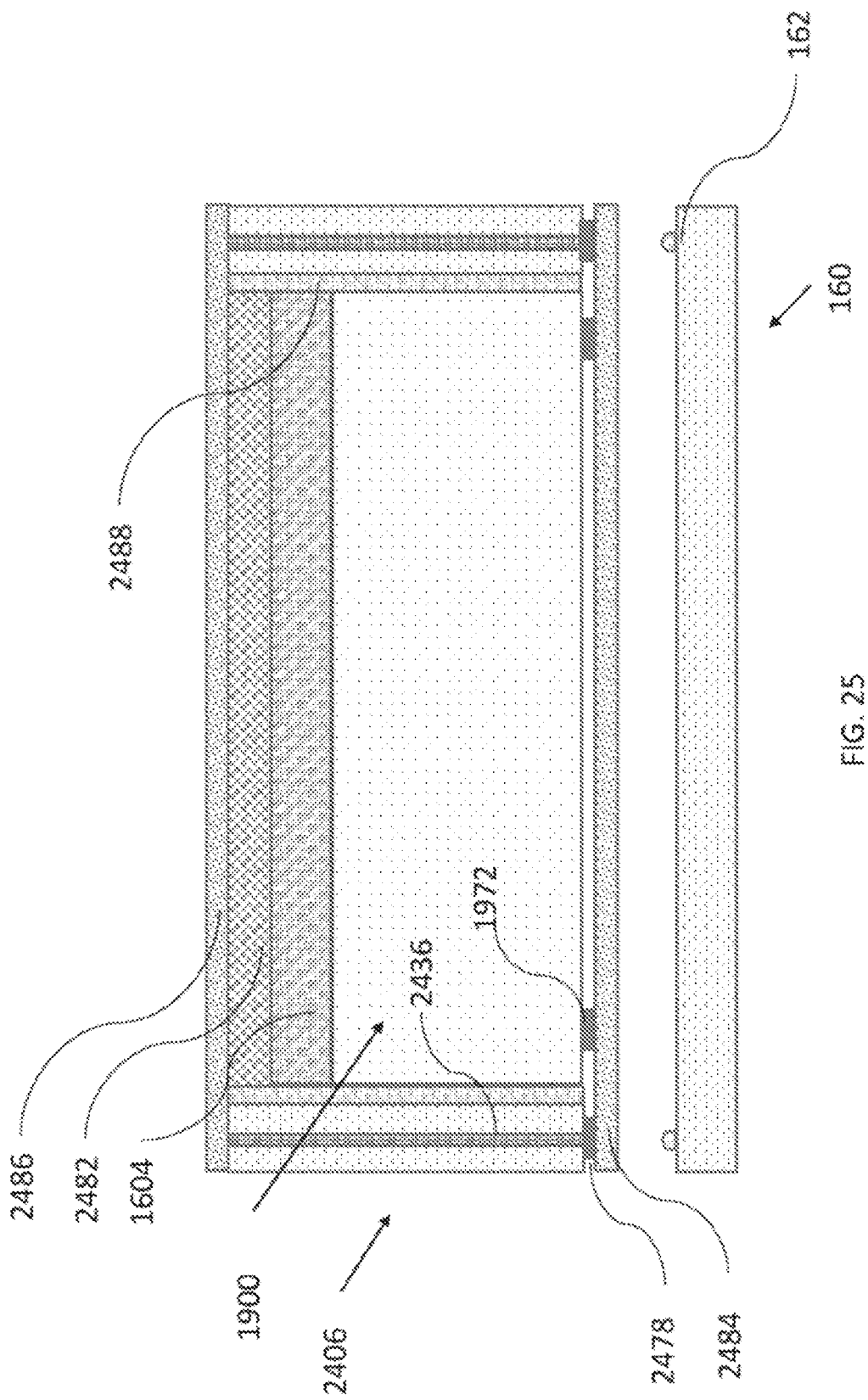
FIG. 25 illustrates another cross-sectional view of the example ultrasound device of FIG. 24 during packaging, in accordance with certain embodiments described herein.

In FIG. 25, the ultrasound-on-a-chip 1900 is coupled to the interposer 2406. The ultrasound-on-a-chip 1900 is inserted in the interposer 2406 such that the face of the ultrasound-on-a-chip 1900 that includes the bond pads 1972 faces the liner 2484. The ultrasound-on-a-chip 1900 is adhered to the interposer 2406 with adhesive 2488. A liner 2486 is placed over the faces of the ultrasound ultrasound-on-a-chip 1900 and interposer 2406 not already covered by the liner 2484.

Figure 26:
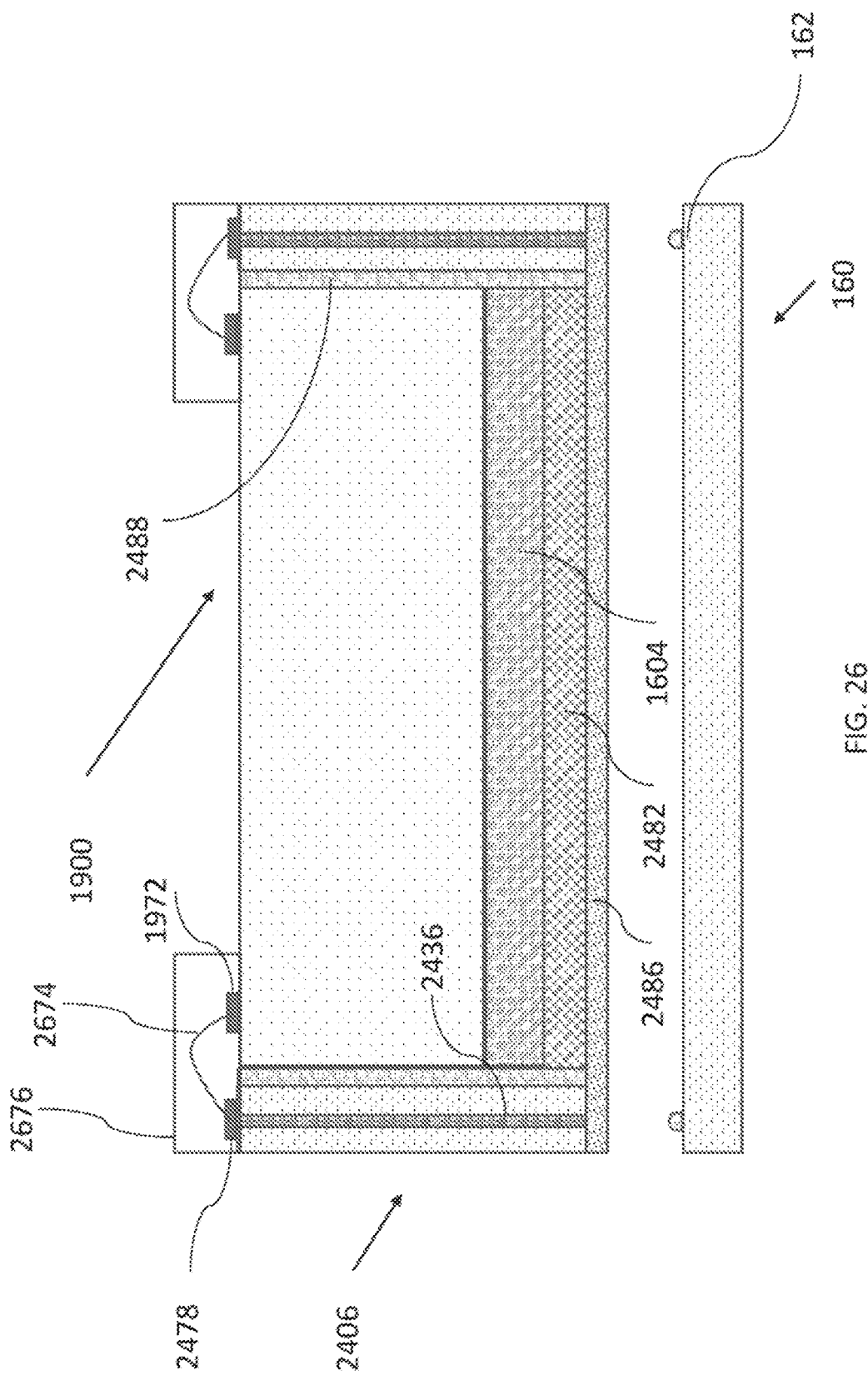
FIG. 26 illustrates another cross-sectional view of the example ultrasound device of FIG. 24 during packaging, in accordance with certain embodiments described herein.

In FIG. 26, the ultrasound-on-a-chip 1900 is wirebonded to the interposer 2406. All the elements in FIG. 26, aside from the PCB 160, are illustrated flipped vertically from the orientation of FIG. 25. FIG. 26 includes wirebonds 2674 and encapsulation 2676. The liner 2484 is removed. The wirebonds 2674 extend between the bond pads 1972 on the ultrasound-on-a-chip 1900 and the bond pads 2478 on the interposer 2406. The encapsulation 2676 encapsulates the wirebonds 2674 and may serve to protect and insulate the wirebonds 2674. It should be appreciated that there may be more wirebonds 2674 than shown.

Figure 27:
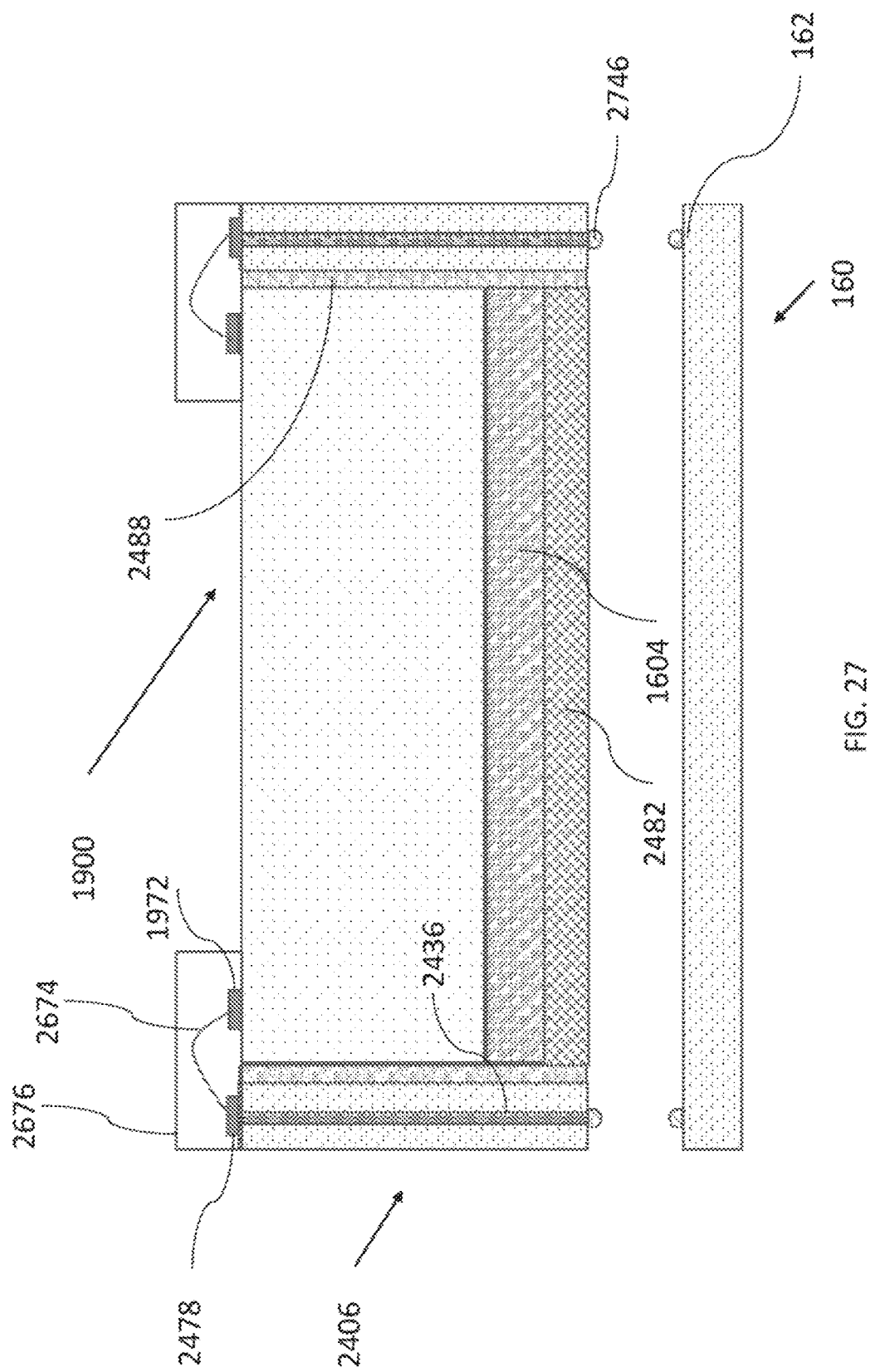
FIG. 27 illustrates another cross-sectional view of the example ultrasound device of FIG. 24 during packaging, in accordance with certain embodiments described herein.

In FIG. 27, the liner 186 has been removed. Solder bumps 2746 have been placed on the interposer 2406 such that the solder bumps 2746 are electrically connected to the vias 2436. Thus, the vias 2436 electrically connect the bond pads 2478 to the solder bumps 2746.

Figure 28:
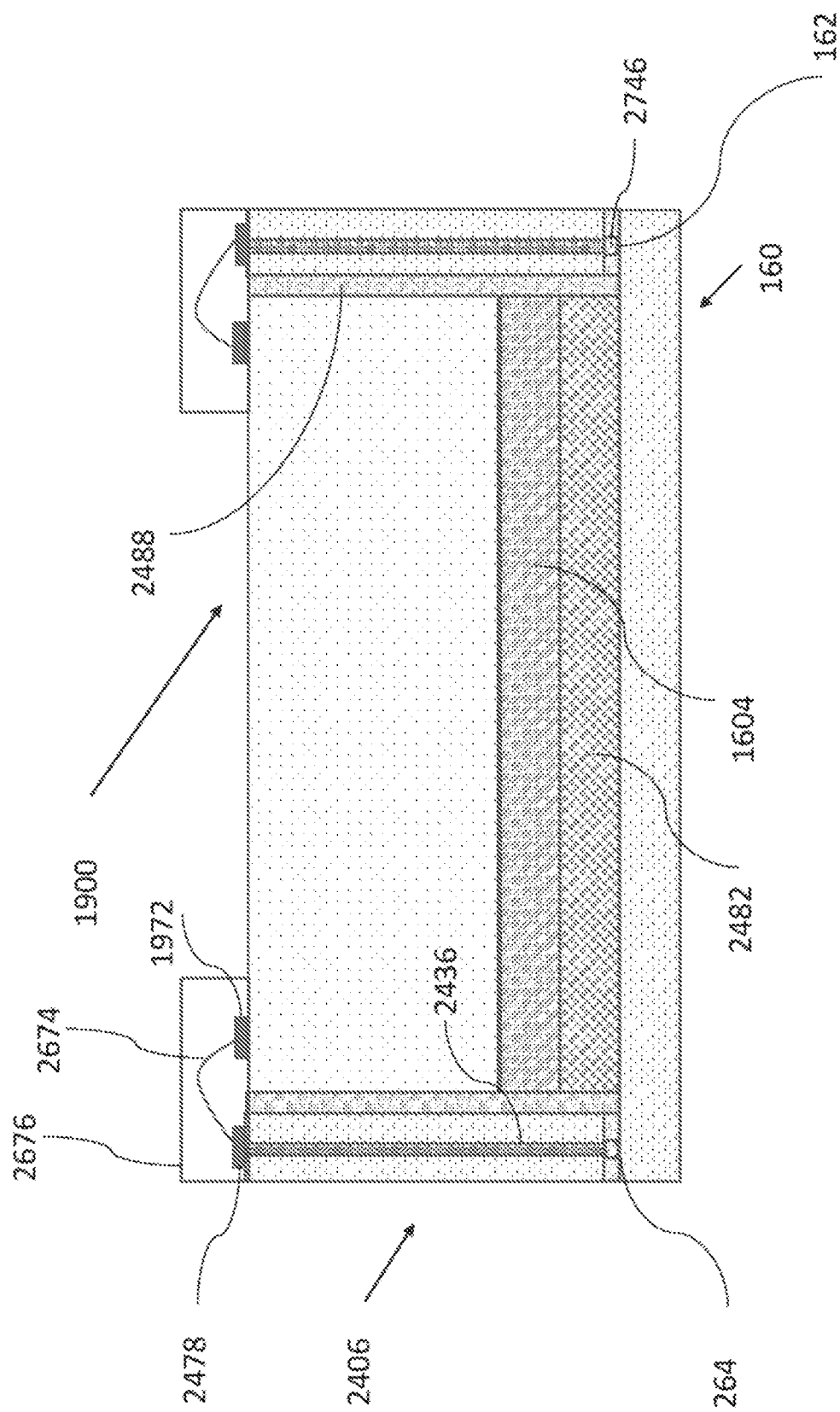
FIG. 28 illustrates another cross-sectional view of the example ultrasound device of FIG. 24 during packaging, in accordance with certain embodiments described herein.

In FIG. 28, the interposer 2406 is coupled to the PCB 160. The interposer 2406 may be bonded to the PCB 160 using a surface-mount technology (SMT) process. In particular, the solder bumps 2746 on the lower surface of the interposer 2406 may be solder bonded to the solder bumps 162 on the upper surface of the PCB 160. Therefore, circuitry and/or traces in the PCB 160 may be electrically connected, through the solder bumps 162 and 146, the vias 2436, the bond pads 2478, the wirebonds 2674, and the bond pads 1972 to integrated circuitry and/or interconnect in the ultrasound-on-a-chip 1900. FIG. 28 further illustrates underfill 264 that has been deposited between the interposer 2406 and the PCB 160. The underfill 264 may help improve the mechanical and thermal properties of the solder bonds between the interposer 2406 and the PCB 160.

Figure 29:
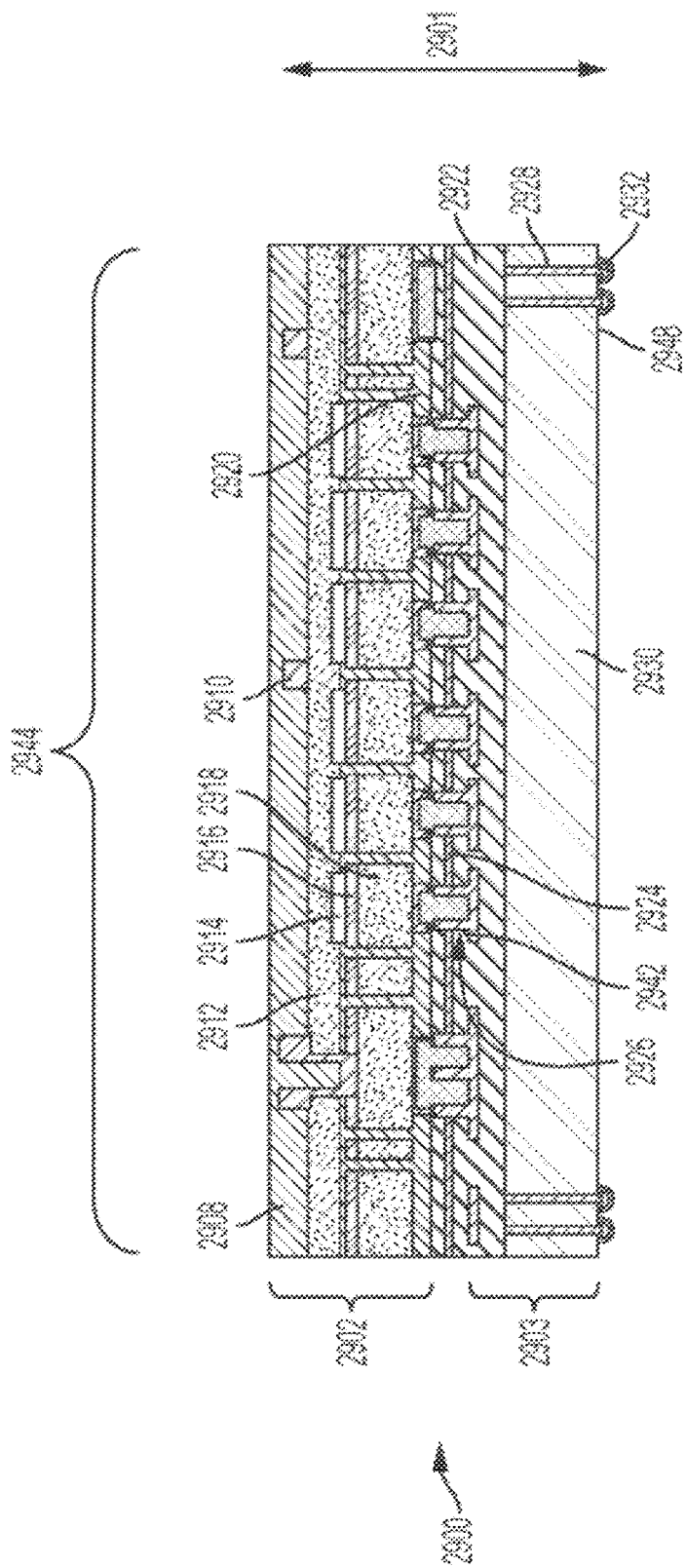
FIG. 29 illustrates an example of an ultrasound-on-a-chip, in accordance with certain embodiments described herein.

FIG. 29 illustrates an example of an ultrasound-on-a-chip 2900, in accordance with certain embodiments described herein. The ultrasound-on-a-chip 2900 includes an ultrasonic transducer substrate 2902 bonded to an integrated circuit substrate 2903, such as a complementary metal oxide semiconductor (CMOS) substrate. The ultrasonic transducer substrate 2902 includes a plurality of cavities 2914, a first silicon device layer 2918, a second silicon device layer 2912, a silicon oxide layer 2920, a passivation layer 2908, silicon oxide portions 2916, and metallization 2910. The cavities 2914 are formed between the first silicon device layer 2918 and the second silicon device layer 2912. The silicon oxide layer 2920 (e.g., a thermal silicon oxide such as a silicon oxide formed by thermal oxidation of silicon) is formed between the first and second silicon device layers 2918 and 2912, with the cavities 2914 being formed therein.

The cavities 2914 may be formed by bonding two substrates including silicon oxide together. The silicon oxide portions 2916 may represent the silicon oxide layer on one substrate that was bonded to the silicon oxide layer 2920 that was on the other substrate prior to bonding. In this non-limiting example, the first silicon device layer 2918 may be configured as a bottom electrode and the second silicon device layer 2912 may be configured as a membrane. Thus, the combination of the first silicon device layer 2918, the second silicon device layer 2912, and the cavities 2914 may form ultrasonic transducers (e.g., capacitive micromachined ultrasonic transducers (CMUTs)), of which six are illustrated in this non-limiting cross-sectional view. To facilitate operation as a bottom electrode or membrane, one or both of the first silicon device layer 2918 and second silicon device layer 2912 may be doped to act as conductors, and in some cases may be highly doped (e.g., having a doping concentration greater than $10^{15}$ dopants/cm$^3$ or greater). The passivation layer 2908 passivates the first silicon device layer 2918. Metallization 2910 provides external electrical contact to the ultrasonic transducers. The upper face 2944 of the ultrasound-on-a-chip represents the face from which ultrasonic energy will be transmitted by the ultrasound transducers for imaging. Therefore, the upper face 2944 represents the sensor face of the ultrasound device of which the ultrasound-on-a-chip 2900 is a part.

The integrated circuit substrate 2903 includes metallization 2942, an insulating layer 2922, a bulk silicon layer 2930, through-silicon vias (TSVs) 2928, and solder bumps 2932. (Solder bumps described herein may be plated and then annealed to form half-dome structures.) The metallization 2942 may be formed of aluminum, copper, or any other suitable metallization material, and may represent at least part of an integrated circuit formed in the integrated circuit substrate 2903. For example, the metallization 2942 may serve as a routing layer, may be patterned to form one or more electrodes, or may be used for other functions. In practice, the integrated circuit substrate 2903 may include more than one metallization layer, but for simplicity only one metallization 2942 is illustrated.

The TSVs 2928 are vias that pass through the bulk silicon layer 2930. The TSVs 2928 may transmit electrical signals between one or more integrated circuits included in the integrated circuit substrate 2903 and the solder bumps 2932, which are on a lower surface 2948 of the ultrasound-on-a-chip 2900 (i.e., the surface opposite the upper surface 2944) and may be external electrical contacts. The TSVs 2928 may be formed for example, from copper, doped polysilicon, or tungsten. (Electrical connection between the TSVs 2928 and integrated circuits in the integrated circuit substrate 2903 are not shown in FIG. 29). In some embodiments, the TSVs 2928 and the solder bumps 2932 may be absent.

The ultrasound-on-a-chip 2900 further includes bonding structures 2926 and a passivation layer 2924 formed in preparation for forming the bonding structures 2926. The bonding structures 2926 electrically connect the ultrasonic transducer substrate 2902 to the integrated circuit substrate 2903. Accordingly, electrical signals may be transmitted from the integrated circuit substrate 2903, through the bonding structures 2926, and to the ultrasonic transducer substrate 2902, and vice versa.

It should be appreciated that when the height 2901 of the ultrasound-on-a-chip 2900 is reduced in accordance with certain embodiments described herein, this may be accomplished by reducing the height of the bulk silicon layer 2930.

Additional information regarding the fabrication and integration of CMUTs with CMOS wafers may be found, for example, in U.S. Pat. No. 9,067,779 titled "MICROFABRICATED ULTRASONIC TRANSDUCERS AND RELATED APPARATUS AND METHODS," granted on Jun. 30, 2015 (and assigned to the assignee of the instant application). However, it should be appreciated that the embodiment shown in FIG. 29 represents just one possible configuration for the ultrasound-on-a-chip 2900. Other configurations are also possible including, but not limited to, a side-by-side arrangement where transducers and integrated circuitry are formed on the same substrate, as well as arrays formed from piezoelectric micromachined ultrasonic transducers (PMUTs), or other suitable types of ultrasonic transducers. In still other embodiments, the ultrasound-on-a-chip device 2900 may include an ultrasonic transducer array by itself (i.e., an ultrasonic transducer chip), where integrated circuitry is located on a different substrate or circuit board altogether.

Figure 30:
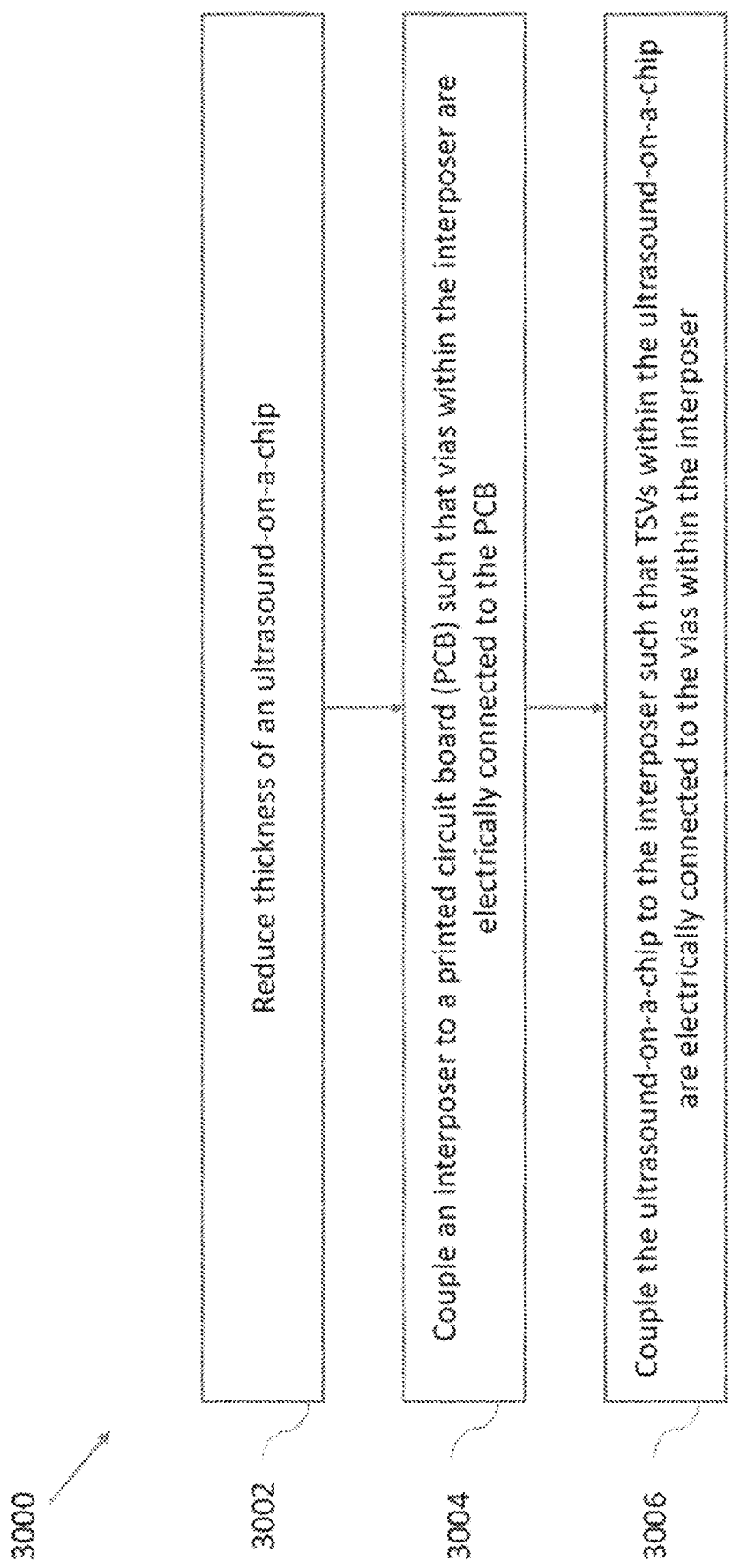
FIG. 30 illustrates an example process for packaging an ultrasound-on-a-chip, in accordance with certain embodiments described herein.

FIG. 30 illustrates an example process 3000 for packaging an ultrasound-on-a-chip, in accordance with certain embodiments described herein. Further description of the process 3000 may be found with reference to FIGS. 1-7 and 16-18.

In act 3002, an ultrasound-on-a-chip is reduced in thickness. In particular, the height of the ultrasound-on-a-chip 100 is reduced after having been fabricated (e.g., using grinding or etching), prior to packaging. In such embodiments, the height of the ultrasound-on-a-chip may be reduced from between or equal to approximately 760-800 microns to between or equal to approximately 200-300 microns. Thinning the ultrasound-on-a-chip may help, during use, to force long-wavelength components of ultrasound waves to exit the ultrasound-on-a-chip, thus reducing spurious acoustic reflections back into the ultrasound-on-a-chip and interference. In some embodiments, act 3002 may be absent, and the ultrasound-on-a-chip may not be reduced in thickness. In such embodiments, the ultrasound-on-a-chip may be coupled to a backing material. The thickness of the backing material 1604 may be between or equal to approximately 400-600 microns, may include an epoxy containing tungsten, and may be screen-printed onto the ultrasound-on-a-chip or an interposer (as described below). The process 3000 proceeds from act 3002 to act 3004.

In act 3004, an interposer is coupled to a printed circuit board, such that vias within the interposer are electrically connected to the PCB. For example, solder bumps on the interposer that are electrically connected to vias within the interposer may be bonded to solder bumps on the PCB. In some embodiments, the interposer includes a heat sink portion including a ceramic material such as aluminum nitride, aluminum oxide, beryllium, and/or low-temperature co-fired ceramic (LTCC), and the vias pass through the heat sink portion. In some embodiments, the interposer includes both a heat sink portion and an electrical connectivity portion, where the electrical connectivity portion includes an organic, glass, or silicon material, and the vias pass through the electrical connectivity portion. In embodiments including a backing material, the backing material may be disposed between the ultrasound-on-a-chip and the interposer. The process 3000 proceeds from act 3004 to act 3006.

In act 3006, the ultrasound-on-a-chip is coupled to the interposer such that TSVs within the ultrasound-on-a-chip are electrically connected to vias within the interposer. For example, solder bumps on the ultrasound-on-a-chip that are electrically connected to the TSVs within the ultrasound-on-a-chip may be bonded to solder bumps on the interposer that are electrically connected to vias within the interposer.

TSVs in the ultrasound-on-a-chip device may be helpful for the following reasons:

1. Compared with other interconnect for electrically connecting the ultrasound-on-a-chip to the external environment that may require longer electrical paths, TSVs may present lower parasitic inductance and resistance, leading to higher power efficiency and less heating of the ultrasound device.

2. Using TSVs may facilitate using a surface mount technology (SMT) process for coupling the ultrasound-on-a-chip to an interposer. It may be possible to solder bond most or all of the solder bumps of the interposer to the solder bumps of the ultrasound-on-a-chip at once, and it may be possible to use a single machine to solder bond multiple ultrasound-on-a-chips to multiple interposers at once. In other words, using TSVs may facilitate a high throughput packaging process that may be better suited for packaging high volumes of ultrasound-on-a-chips.

3. During ultrasound imaging, the upper face of the ultrasound-on-a-chip may be pressed against a subject. (It should be noted that one or more structures, such as an acoustic lens, may be disposed between the upper face of the ultrasound-on-a-chip and the subject during imaging.) The TSVs are not disposed near the upper face of the ultrasound-on-a-chip and accordingly may be less subject to damage due to this pressure.

4. Other interconnect structures for electrically connecting to the ultrasound-on-a-chip may extend laterally from the upper face of the ultrasound-on-a-chip. Accordingly, the upper face of the packaged ultrasound-on-a-chip may be larger in size than the upper face of the ultrasound-on-a-chip itself due to this lateral extension. As discussed above, TSVs are not disposed near the upper face of the ultrasound-on-a-chip, and therefore do not contribute significantly to the size of the upper face of the ultrasound-on-a-chip. Avoiding increasing the size of the upper face of the packaged ultrasound-on-a-chip with interconnect may help to reduce the overall size of the ultrasound device and enable form factors for the ultrasound device such as ultrasound patches. Additionally, avoiding increasing the size of the upper face of the packaged ultrasound-on-a-chip with interconnect may, for example, help the upper face of the packaged ultrasound-on-a-chip fit between a subject's ribs during imaging. This may be especially helpful for cardiac imaging. Additionally, avoiding increasing the size of the upper face of the packaged ultrasound-on-a-chip with interconnect may help to reduce the amount of acoustic lens material that is deposited on the upper face of the packaged ultrasound-on-a-chip. In particular, reducing the thickness of the acoustic lens material may help to reduce attenuation of pressure waves generated by the ultrasound device.

In some embodiments, act 3006 may be performed prior to act 3004. In other words, the interposer may be coupled to the ultrasound-on-a-chip before being coupled to the PCB. In some embodiments, act 3004 may be absent, and in such embodiments, the interposer may be coupled to another type of device, or not coupled to another device.

Figure 31:
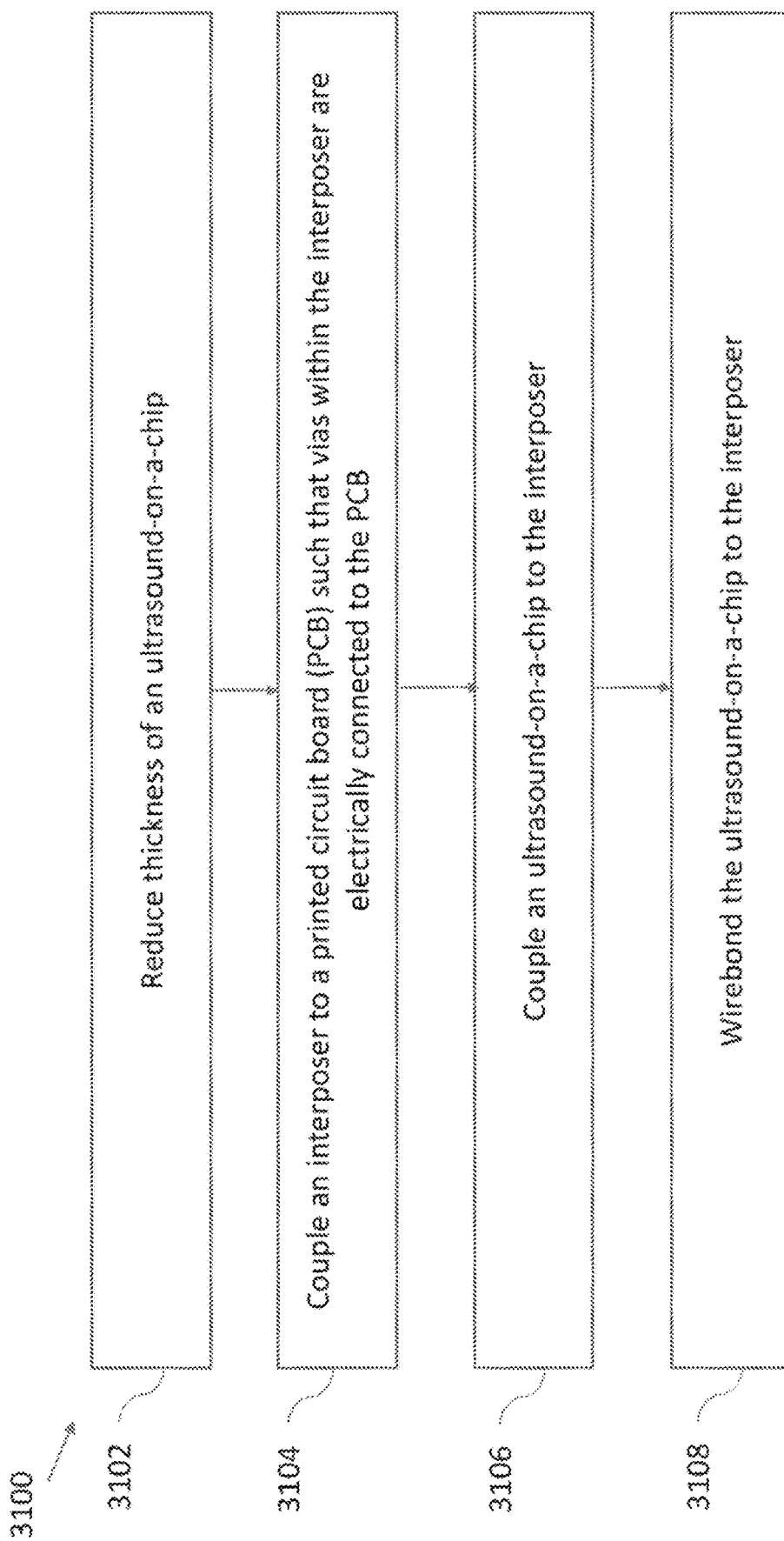
FIG. 31 illustrates an example process for packaging an ultrasound-on-a-chip, in accordance with certain embodiments described herein.

FIG. 31 illustrates another example process 3100 for packaging an ultrasound-on-a-chip, in accordance with certain embodiments described herein. Further description of the process 3100 may be found with reference to FIGS. 8-11, 19-22, and 24-28.

In act 3102, an ultrasound-on-a-chip is reduced in thickness. Further description of the act 3102 may be found with reference to act 3002. As described above, in some embodiments act 3102 may be absent. The process 3100 proceeds from act 3102 to act 3104.

In act 3104, an interposer is coupled to a printed circuit board, such that vias within the interposer are electrically connected to the PCB. Further description of the act 3104 may be found with reference to act 3004. The process 3100 proceeds from act 3104 to act 3106.

In act 3106, the ultrasound-on-a-chip is coupled to the interposer. For example, the ultrasound-on-a-chip may be coupled to the interposer through adhesive. The process 3100 proceeds from act 3106 to act 3108.

In some embodiments, act 3106 may be performed prior to act 3104. In other words, the interposer may be coupled to the ultrasound-on-a-chip before being coupled to the PCB. In some embodiments, act 3104 may be absent, and in such embodiments, the interposer may be coupled to another type of device, or not coupled to another device.

In act 3108, the ultrasound-on-a-chip is wirebonded to the interposer. For example, wirebonds may extend from bond pads on the ultrasound-on-a-chip to bond pads on the interposer. When the wirebonds extend from the ultrasound-on-a-chip to the interposer, the wirebonds may be shorter than wirebonds extending from the ultrasound-on-a-chip to the PCB. The shorter wirebonds may result in a smaller upper face of the packaged ultrasound-on-a-chip, which may help to reduce the overall size of the ultrasound device, may help the upper face of the packaged ultrasound-on-a-chip fit between a subject's ribs during imaging, and may help to reduce the amount of acoustic lens material that is deposited on the upper face of the packaged ultrasound-on-a-chip.

Figure 32:
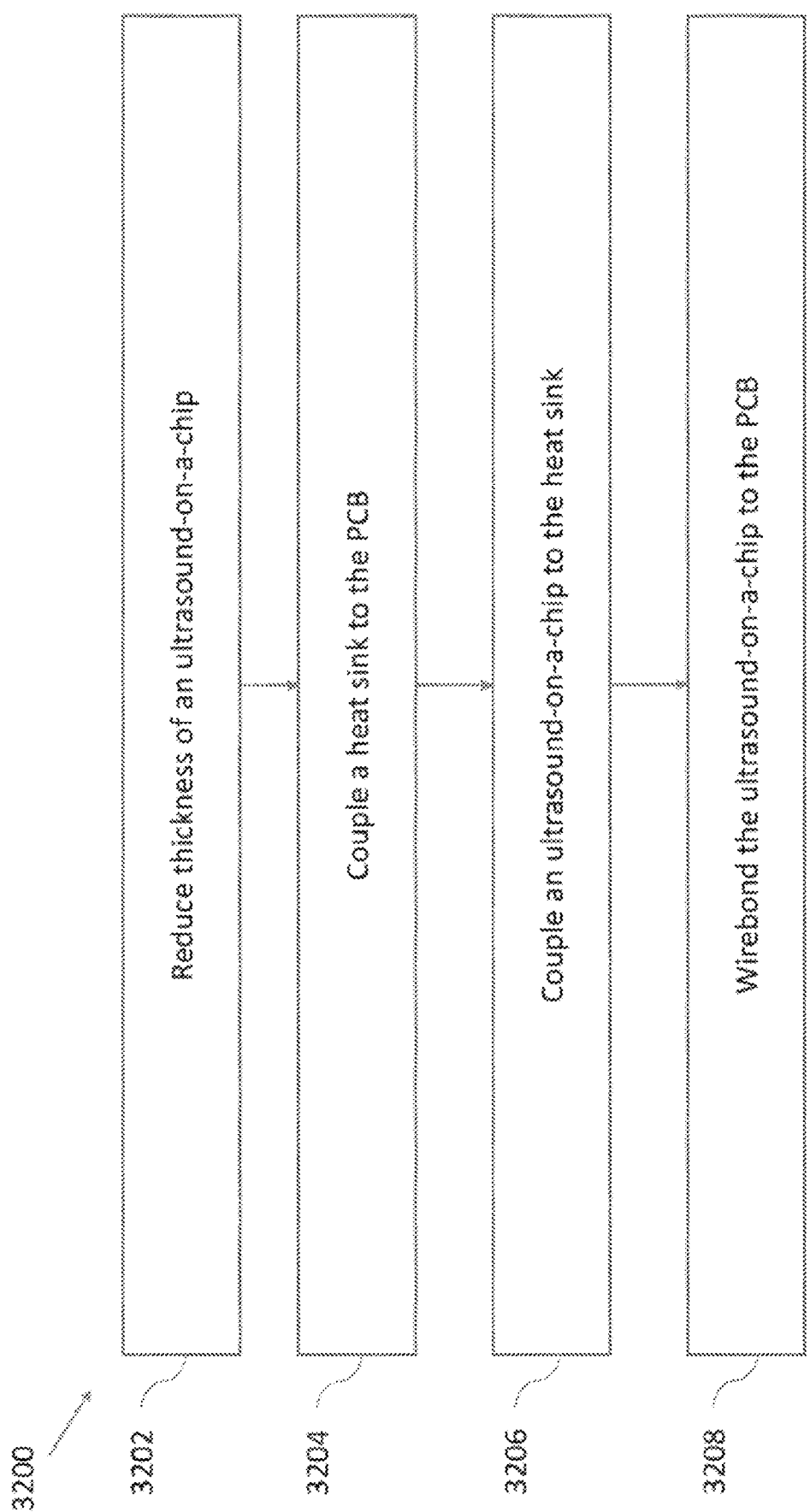
FIG. 32 illustrates an example process for packaging an ultrasound-on-a-chip, in accordance with certain embodiments described herein.

FIG. 32 illustrates another example process 3100 for packaging an ultrasound-on-a-chip, in accordance with certain embodiments described herein. Further description of the process 3200 may be found with reference to FIGS. 12-15.

In act 3202, an ultrasound-on-a-chip is reduced in thickness. Further description of the act 3202 may be found with reference to act 3002. The process 3200 proceeds from act 3202 to act 3204.

In act 3204, a heat sink is coupled to a printed circuit board (PCB). For example, the heat sink may be coupled to the printed circuit board by surface mount technology. The process 3200 proceeds from act 3204 to act 3206.

In act 3206, the ultrasound-on-a-chip is coupled to the heat sink. For example, the ultrasound-on-a-chip may be coupled to the heat sink through adhesive or surface mount technology. The heat sink may include a ceramic material such as aluminum nitride, aluminum oxide, beryllium, and/or low-temperature co-fired ceramic (LTCC). The process 3200 proceeds from act 3206 to act 3208.

In some embodiments, act 3206 may be performed prior to act 3204. In other words, the heat sink may be coupled to the ultrasound-on-a-chip before being coupled to the PCB. In some embodiments, act 3204 may be absent, and the heat sink may be coupled to another type of device, or not coupled to another device.

In act 3208, the ultrasound-on-a-chip is wirebonded to the PCB. For example, wirebonds may extend from bond pads on the ultrasound-on-a-chip to bond pads on the PCB. When the wirebonds extend from the ultrasound-on-a-chip to the PCB, the heat sink may not include vias as other interposers do, such as those described with reference to processes 3000 and 3100.

While the above description has described packaging schemes that may be used for an ultrasound-on-a-chip, it should be appreciated that the packaging schemes may be used for other types of dies as well. For example, any of the interposers described herein may be used in conjunction with other types of dies.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. A portable ultrasound imaging device, comprising:
a hand-held ultrasound probe; and
an ultrasound-on-a-chip package housed in the handheld ultrasound probe, the ultrasound-on-a-chip package comprising:
an ultrasound-on-a-chip; and
an interposer coupled to the ultrasound-on-a-chip, the interposer comprising:
a plurality of first vias electrically coupled to the ultrasound-on-a-chip; and
a plurality of second vias different than the plurality of first vias and configured to conduct heat away from the ultrasound-on-a-chip.

2. The portable ultrasound imaging device of claim 1, wherein the plurality of second vias are coupled to copper patterns disposed on a face of the interposer and protruding towards the ultrasound-on-a-chip from the face of the interposer.

3. The portable ultrasound imaging device of claim 1, wherein an adhesive is disposed along a portion of an interface between the ultrasound-on-a-chip and the interposer.

4. The portable ultrasound imaging device of claim 1, wherein a thermally conductive material is disposed along a portion of an interface between the ultrasound-on-a-chip and the interposer.

5. The portable ultrasound imaging device of claim 1, wherein a thickness of the ultrasound-on-a-chip is about 200 microns to 300 microns.

6. The portable ultrasound imaging device of claim 1, wherein vias of the plurality of first vias are electrically coupled to the ultrasound-on-a-chip by wirebonds.

7. The portable ultrasound imaging device of claim 1, wherein the ultrasound-on-a-chip and the interposer are coupled together using a surface-mount technology (SMT) process.

8. The portable ultrasound imaging device of claim 1, further comprising a printed circuit board comprising circuitry and/or traces, the printed circuit board being coupled to the interposer such that the plurality of first vias in the interposer are electrically connected to the circuitry and/or traces in the printed circuit board.

9. A portable ultrasound imaging device, comprising:
a hand-held ultrasound probe; and
an ultrasound-on-a-chip package housed in the hand-held ultrasound probe, the ultrasound-on-a-chip package comprising:
an ultrasound-on-a-chip including first bond pads;

an interposer comprising second bond pads and coupled to the ultrasound-on-a-chip; and wirebonds extending from the first bond pads on the ultrasound-on-a-chip to the second bond pads on the interposer.

10. The portable ultrasound imaging device of claim 9, the interposer further comprising:

a plurality of first vias electrically coupled to the second bond pads; and a plurality of second vias different than the plurality of first vias and configured to conduct heat away from the ultrasound-on-a-chip.

11. The portable ultrasound imaging device of claim 10, wherein the plurality of second vias are coupled to copper patterns disposed on a face of the interposer and protruding towards the ultrasound-on-a-chip from the face of the interposer.

12. The portable ultrasound imaging device of claim 10, wherein an empty space exists along a portion of an interface between the ultrasound-on-a-chip and the interposer.

13. The portable ultrasound imaging device of claim 10, wherein an adhesive is disposed along a portion of an interface between the ultrasound-on-a-chip and the interposer.

14. The portable ultrasound imaging device of claim 10, wherein a thermally conductive material is disposed along a portion of an interface between the ultrasound-on-a-chip and the interposer.

15. The portable ultrasound imaging device of claim 10, further comprising a printed circuit board comprising circuitry and/or traces, and wherein the printed circuit board is coupled to the interposer such that the plurality of first vias in the interposer are electrically connected to the circuitry and/or traces in the printed circuit board.

* * * * *